(12) United States Patent
Persson

(10) Patent No.: US 8,841,081 B2
(45) Date of Patent: Sep. 23, 2014

(54) METHOD OF TREATING METASTATIC STAGE PROSTATE CANCER

(75) Inventor: Bo-Eric Persson, Rolle (CH)

(73) Assignee: Ferring International SA, Saint-Prex (CH)

( * ) Notice: Subject to any disclaimer, the term of this patent is extended or adjusted under 35 U.S.C. 154(b) by 149 days.

(21) Appl. No.: 12/368,713

(22) Filed: Feb. 10, 2009

(65) Prior Publication Data

US 2009/0203622 A1 Aug. 13, 2009

Related U.S. Application Data

(60) Provisional application No. 61/027,741, filed on Feb. 11, 2008, provisional application No. 61/147,956, filed on Jan. 28, 2009.

(30) Foreign Application Priority Data

Feb. 29, 2008 (EP) .................................... 08250703

(51) Int. Cl.
*G01N 33/574* (2006.01)
*A61K 38/09* (2006.01)

(52) U.S. Cl.
CPC ...................................... *A61K 38/09* (2013.01)
USPC .............................................. 435/7.23; 514/1

(58) Field of Classification Search
None
See application file for complete search history.

(56) References Cited

U.S. PATENT DOCUMENTS

| | | | |
|---|---|---|---|
| 3,773,919 | A | 11/1973 | Boswell |
| 5,506,207 | A | 4/1996 | Rivier et al. |
| 5,516,887 | A | 5/1996 | Deghenghi |
| 5,595,760 | A | 1/1997 | Cherif-Cheikh |
| 5,821,230 | A | 10/1998 | Jiang et al. |
| 5,860,957 | A | 1/1999 | Jacobsen et al. |
| 5,863,549 | A | 1/1999 | Tarantino |
| 5,925,730 | A | 7/1999 | Semple et al. |
| 6,214,798 | B1 | 4/2001 | Semple et al. |
| 6,503,534 | B1 | 1/2003 | Pellet et al. |
| 2004/0038903 | A1 | 2/2004 | Luck et al. |
| 2004/0138610 | A1 | 7/2004 | Cormier et al. |
| 2005/0245455 | A1 | 11/2005 | Luck et al. |
| 2006/0135405 | A1 | 6/2006 | Rischer et al. |
| 2009/0018085 | A1 | 1/2009 | Luck et al. |
| 2009/0203622 | A1 | 8/2009 | Persson |
| 2009/0209939 | A1 | 8/2009 | Verespej et al. |
| 2010/0286603 | A1 | 11/2010 | Winderstrom |
| 2010/0305042 | A1 | 12/2010 | Olesen et al. |
| 2011/0039787 | A1 | 2/2011 | Petri et al. |
| 2011/0053846 | A1 | 3/2011 | Luck et al. |
| 2012/0172302 | A1 | 7/2012 | Petri et al. |
| 2013/0018223 | A1 | 1/2013 | Joseph |
| 2013/0029910 | A1 | 1/2013 | Meulen et al. |
| 2013/0281661 | A1 | 10/2013 | Rasmusse et al. |
| 2013/0281662 | A1 | 10/2013 | Kalita et al. |
| 2013/0295166 | A1 | 11/2013 | Grenier et al. |

FOREIGN PATENT DOCUMENTS

| | | |
|---|---|---|
| CN | 1411803 A | 4/2003 |
| EP | 0 002 749 B1 | 10/1983 |
| EP | 0 556 034 A1 | 8/1993 |
| EP | 1 003 774 B1 | 5/2000 |
| EP | 1 967 202 A1 | 9/2008 |
| FR | 2 776 520 A | 10/1999 |
| WO | WO 03/006049 A1 | 1/2003 |
| WO | WO 2004/080413 A2 | 9/2004 |
| WO | WO 2007/130809 A2 | 11/2007 |
| WO | WO 2008/135989 | 11/2008 |
| WO | WO 2009/101533 A1 | 8/2009 |
| WO | WO 2011/004260 A2 | 1/2011 |

OTHER PUBLICATIONS

Gittelman et al, J Urol. 2008, 180:1986-1992.*
Van Poppel et al, Eur Urol. Suppl, 2006, 5(2):251.*
Demers et al, Cancer, 2000, 88:2919-2926.*
Hegel et al, BJU Int, 2006, 99:330-334.*
Albertsen, et al. "Cardiovascular Morbidity Associated with Gonadotropin Releasing Hormone Agonist and an Antagonist," European Urology (2013), https://dx.doi.org/10.16/j.eururo.2013.10,032.
Office Action (final) dated Jan. 9, 2014, U.S. Appl. No. 12/829,467.
Office Action (final) dated Oct. 8, 2013, U.S. Appl. No. 13/381,762.
Office Action dated Jun. 6, 2013, U.S. Appl. No. 12/774,113.
Office Action dated Sep. 11, 2013, in U.S. Appl. No. 12/771,199.
Office Action dated Sep. 3, 2013, in U.S. Appl. No. 13/458,330.
The K-Zone, Biophysical data tables: standard man, Jul. 2004; printed Mar. 14, 2009 from www.kevinboone.com/biodat_stdman.html; 1 page.
SEER Progam and the National Center for Health Statistics, <http://seer.cancer.gov/.>, 2008.
Cancer Trends Progress Report, http://progressreport.cancer.gov, 2008.
Granfors, et al., "Combined Orchiectomy and External Radiotherapy Versus Radiotherapy Alone for Nonmetastatic Prostate Cancer With or Without Pelvic Lymph Node Involvement: A Prospective Randomized Study," *J. Urol.*, (1998), 159:2030-34.
Messing, et al., "Immediate Hormonal Therapy Compared with Observation after Radical Prostatectomy and Pelvic Lymphadenectomy in Men with Node-Positive Prostate Cancer," (1999) *N. Eng. J. Med.*, vol. 341, pp. 1781-1788.
Kirk, et al., "Immediate versus deferred treatment for advanced prostatic cancer: initial results of the Medical Research Counsel trial," *British Journal of Urology*, (1997) vol. 79, pp. 235-246.
Thompson, et al., "Sudden Death to Disease Flare With Luteinizing Hormone-Releasing Hormone Agonist Therapy for Carcinoma of the Prostate," *J. Urol.*, (1990) vol. 144, pp. 1479-1480.

(Continued)

*Primary Examiner* — Mark Halvorson
(74) *Attorney, Agent, or Firm* — Finnegan, Henderson, Farabow, Garrett and Dunner, L.L.P.

(57) ABSTRACT

The invention provides methods and dosing regimens for treating metastatic stage prostate cancer in a subject using degarelix, as well as related methods of using degarelix in a subject identified as having metastatic stage prostate cancer, and methods of using degarelix to prevent or delay the progression of locally advanced prostate cancer.

18 Claims, 11 Drawing Sheets

(56) References Cited

OTHER PUBLICATIONS

Boccon-Gibod, et al., "Cyproterone Acetate Lead-In Prevents Initial Rise of Serum Testosterone Induced by Luteinizing Hormone-Releasing Hormone Analogs in the Treatment of Metastatic Carcinoma of the Prostate," (1986) *Eur. Urol.*, vol. 12, pp. 400-402.
Yannucci, et al., "The Effect of Androgen Deprivation Therapy on Fasting Serum Lipid and Glucose Parameters," (2006) *J. Urol.*, vol. 176, pp. 520-525.
Etzioni, et al., "Cancer Surveillance Series: Interpreting Trends in Prostate Cancer-Part III: Quantifying the Link Between Population Prostate-Specific Antigen Testing and Recent Declines in Prostate Cancer Mortality," (1999) *J. Natl. Canc. Inst.*, vol. 91, pp. 1033-1039.
Persad, "Leuprorelin Acetate in Prostate Cancer: A European Update," (2002) *Int. J. Clin. Pract.*, vol. 56, No. 5, pp. 389-396.
Wilson, et al., "Leuprolide acetate: a drug of diverse clinical applications," *Expert Opin. Investig. Drugs*, (2007), vol. 16, pp. 1851-1863.
Berges, et al., "Effect of a new leuprorelin formulation on testosterone levels in patients with advanced prostate cancer," (2006), *Cur. Med. Res. Opin.*, vol. 22, No. 4, pp. 649-655.
Mongiat-Artus, et al., "Abarelix: the first gonadotrophin-releasing hormone antagonist for the treatment of prostate cancer," (2004), *Expert Opin. Pharmacother*, vol. 5, pp. 2171-2179.
Debruyne, et al., "Abarelix for injectable suspension: first-in-class gonadotropin-releasing hormone antagonist for prostate cancer," (2006) *Future Oncol.*, vol. 2, pp. 677-696.
Spilker, Bert, "Guide to Cinical Trials," (1991) *Raven Press, Ltd.*, New York, ISBN 0-88167-767-1.
Spilker, Bert, "Quality of Life and Pharmacoeconomics in Clinical Trials," (1996) *Lippincott—Raven Publishers*, New York, ISBN 0-7817-0332-8.
Jiang, et al., "GnRH Antagonists: A New Generation of Long Acting Analogues Incorporating *p*-Ureido-phenylalanies at Positions 5 and 6," (2001) *J. Med. Chem.*, vol. 44, pp. 453-467.
Gillum, T., "The Merck Regulatory Dictionary: A Pragmatically Develop Drug Effects Vocabulary," (1989) *Drug Info. J.*, vol. 23, pp. 217-220.
Saltzman, A., "Adverse Reaction Terminology Standardization: A Report on Schering-Plough's Use of the WHO Dictionary and the Formation of the WHO Adverse Reaction Terminology Users Group (WUG) Consortium," (1985) *Drug Info. J.*, vol. 19, pp. 35-41.
McNeil, et al., "On the Elicitation of Preferences for Alternative Therapies," (1982) *N. Engl. J. Med.*, vol. 306, No. 21, pp. 1259-1262.
Teal, et al., "Adverse Drug Experience Management: A Brief Review of the McNeil Pharmaceutical System," (1985) *Drug Info. J.*, vol. 19, pp. 17-25.
Forbes, et al., "FDA's Adverse Drug Reaction Drug Dictionary and Its Role in Post-Marketing Surveillance," (1986) *Drug Inf. J.*, vol. 20, pp. 135-145.
Turner, et a., "The Processing of Adverse Reactoin Reports at FDA," (1986) *Drug. Inf. J.*, vol. 20, pp. 147-150.
Stephens, M.D.B., "The Detection of New Adverse Drug Reactions," (1988) *Stockton Press*, New York, ISBN 0-333-45417-0.
MedDRA website, http://www.meddramsso.com.
Wilson, et al., "Prediction of Coronary Heart Disease Using Risk Factor Categories," (1998) *Circulation*, 97:1837-47.
Hackman, et al., "Emerging Risk Factors for Atheroslerotic Vascular Disease," (2003), *JAMA*, vol. 290, pp. 932-940.
Behn, et al., "The obesity epidemic and its cardiovascular consequences," (2006) *Curr. Opin. Cardiol.* vol. 21, pp. 353-360.
Romero-Corral, et al., "Association of bodyweight with total mortality and with cardiovascular events in coronary artery disease: a systematic review of cohort studies," (2006) *Lancet*, 368:666-678.
http://www.fda.gov/cder/drug/infopage/planaxis/default.htm, 2004.
Gerlinger, et al.,"Recommendation for Confidence interval and sample size calculations for the Pearl Index," (2003) *The European Journal of Contraception and Reproductive Health Care*, vol. 8, pp. 87-92.

Lehmann, "Testing Statistical Hypotheses," (1986) *Second Edition, John Wiley & Sons*, New York, ISBN 0-471-84083-1.
Ferlay,et al., "Estimates of the cancer incidence and mortality in Europe in 2006," *Annals of Oncology*, vol. 18, pp. 581-592 (2007).
Lukka, et al., "Maximal androgen blockade for the treatment of metastatic prostate cancer—a systematic review," *Current Oncology*, vol. 13, No. 3, pp. 81-93, 2006.
Denis, et al., "Overview of Phase III Trials on Combined Androgen Treatment in Patients with Metastatic Prostate Cancer," (1993) *Cancer*, vol. 72, pp. 3888-3895.
Hellerstedt, et al., "The Current State of Hormonal Therapy for Prostate Cancer," *CA A Cancer Journal for Clinicians*, vol. 52, pp. 154-179, 2008.
Chernecky, and Berger, "Laboratory Tests and Diagnostic Procedures," (2008) *Fifth Edition, WB Saunders & Company*, Philadelphia. ISBN-978-1-14160-3704-0.
Fleming,et al., "Post-therapy changes in PSA as an outcome measure in prostate cancer clinical Trials," (2006) *Nature Clinical Practice Oncolology*, vol. 3, No. 12, pp. 658-667.
Lilja, et al., "Prostate-specific antigen and prostate cancer: prediction, detection and monitoring," (2008) *Nature Reviews/Cancer*, vol. 8, pp. 268-278.
Co-pending U.S. Appl. No. 12/155,897, filed Jun. 11, 2008.
Co-pending U.S. Appl. No. 13/381,762, filed Mar. 2012.
Co-pending U.S. Appl. No. 13/458,330, filed Apr. 2012.
Co-pending U.S. Appl. No. 13/881,744, filed Jul. 2013.
Co-pending U.S. Appl. No. 13/881,751, filed Jul. 2013.
Crawford et al., "Long term tolerability and efficacy of degarelix: 5-year results from a phase III extension trial with a one-arm crossover from leuprolide to degarelix", Urologic Oncology, School of Medicine, University of Colorado Denver, pp. 1-18, 2014.
FDA.GOV, Label for Degarelix for injection (Dec. 24, 2008), available at www.accessdata.fda.gov/drugsatfda_docs/label/2008/022201lbl.pdf, last visited Jun. 4, 2013.
Heidenreich et al., "Welche Mechanismen Liegen Der Besseren Kontrolle Des Psa-Progressionsfreien Uberlebens Von Degarelix Im Vergleich Mit Leuprorelin Zudrunde?", RWTH, Aache, Ferring Arzneimittel GmbH, Kiel, 4 pages, 2013.
International Search Report issued on Apr. 19, 2012, in Application No. PCT/EP2012/050695.
Iversen et al., "Improved outcomes with degarelix monotherapy compared with luteinizing hormone-releasing hormone (LHRH) agonists plus antiandrogen in the treatment of men with advanced prostate cancer", 29th Congress of the Scandinavian Association of Urologiest, May 22, 2013, 2 pages.
Malkin, "Are techniques used for intramuscular injection based on research evidence?" Nursingtimes.net, Nursing Times; 104; 50/51, 48-51 Dec. 16, 2008.
Office Action dated Jul. 25, 2013, U.S. Appl. No. 12/829,467.
Office Action dated Jul. 26, 2013, U.S. Appl. No. 12/901,270.
Office Action dated Jun. 11, 2013, U.S. Appl. No. 13/381,762.
People's Republic of China First Office Action dated Feb. 25, 2013 in corresponding Application No. 201080019696.2, 2 pages.
Wiegel et al., "Neoadjuvant Androgen Deprivation Therapy of Prostate Volume Reduction, Lower Urinary Tract Symptom Relief and Quality of Life Improvement in Men with Intermediate-to-High-risk Prostate Cancer: A Randomised Non-inferiority Trial of Degarelix versus Goserelin plus Bicalutamide", 2 pages.
Wolff et al., "Cumulative analysis from six comparative randomised clinical trials of degarelix versus luteinising hormone-releasing hormone (LHRH) agonists: Better PSA-progressionfree survival confirmed in trials an everyday practice", Gerring Arzneimittel GmbH, Kiel, 2 pages.
"Alkaline Phosphatase," GP Notebook (Sep. 12, 2011), http://gpnotebook.co.uk/simplepage.cfm?ID=~1932525548.
Agerso, et al., "The dosing solution influence on the pharmacokinetic of degarelix, a new GnRH0 antagonist, after s.c. administration to beagle dogs," European Journal of Pharmacuetical Sciences, vol. 20, pp. 335-340, 2003.
Albertsen et al.., Reduced Risk of Cardiovascular (CV) Events and Death in Patients (PTS) Receiving Degarelix Compared with LHRH Agonists (2012).

(56) References Cited

OTHER PUBLICATIONS

'Bone Specific Alkaline Phosphatase,' The University of Iowa (UIHC), Dep. of Pathology, Laboratory Services Handbook (Sep. 11, 2011), http://www.healthcare.uiowa.edu/path_handbook/handbook/test2238.html.
Broqua et al., "Effects of the New GNRH Antagonist FE200486 one the Growth of the Androgen-Dependent Prostate Tumor Dunning R-3327H, 6th International Symposium on GnRH Analogues in Cancer and Human Reproduction," Geneva, Switzerland,Feb. 8, 2001.
Broqua, et al., "Pharmacological Profile of a New, Potent, and Long-Acting Gonadotropin-Releasing Hormone Antagonist: Degarelix," The Journal of Pharmacology and Experimental Therapeutics, vol. 301, pp. 95-102, 2002.
Cerotide TM package insert (Aug. 11, 2000).
Co-pending U.S. Appl. No. 12/368,713.
Co-pending U.S. Appl. No. 12/368,935, filed Feb. 2009.
Co-pending U.S. Appl. No. 12/771,199, filed Apr. 2010.
Co-pending U.S. Appl. No. 12/774,113, filed May 2010.
Co-pending U.S. Appl. No. 12/829,467, filed Jul. 2010.
Co-pending U.S. Appl. No. 12/901,270, filed Oct. 2010.
Crawford et al., "A Phase III Extension Trial With a 1-Arm Crossover From Leuprolide to Degarelix: Comparison of Gonadotropin-Releasing Hormone Agonist and Antagonist Effect of Prostate Cancer," 186 The Journal of Urology 889-897 (2011).
Crawford et al., Degarelix Versus LHRH Agonists: Differential Skeletall Morbidity Outcomes from a Pooled Analysis of Six Comparative Randomised Clinical Trials (2012).
de la Rosette et al., "Efficacy and safety of androgen deprivation therapy after switching from monthly leuprolide to monthly degarelix in patients with prostate cancer," 65(5) International Journal of Clinical Practice 559-66 (2011).
de Pinieux, et al., "Clinical and Experimental Progression of a New Model of Human Prostate Cancer and Therapeutic Approach," American Journal of Pathology, vol. 159, No. 2, Aug. 2001.
Eastman et al., "Serum Alkaline Phosphatase: Normal Values by Sex and Age," 23 (9) Clinical Chemistry 1769-1770 (1977).
European Search Report & Opinion, dated Oct. 2, 2012, EP Application No. 12168495.5.
FDA Drug Information Page—Plenaxis (abarelix for injectable suspension); http://www.fda.gov/cder/drug/infopage/planaxis/default.htm, Feb. 2004.
International Search Report issued on Sep. 12, 2002, in Application No. PCT/GB02/03116.
Jiang et al., "Betidamino Acid-Scan of the GNRH Antagonist Acyline," Journal of Medicinal Chemistry, American Chemical Socitey, Washington, US, vol. 40, 1997, pp. 3739-3748.
Lyseng-Williamson, Katherine A., "Degarelix: a guide to its use in advanced prostate cancer," 28(5) Drugs Ther. Perspect. 6-10 (2012).
Miller et al., Differential outcomes from an analysis of six comparative randomised clinical trials of degarelix versus luteinising hormone-releasing hormone (LHRH) agonists) (2012).
Miller et al., "Disease control-related outcomes from an analysis of six comparative randomised clinical trials of degarelix versus luteinising hormone-releasing hormone (LHRH) agonists," (2012).
Office Action mailed Jan. 31, 2013, in copending U.S. Appl. No. 12/901,270.
Office Action mailed Mar. 8, 2011, in copending U.S. Appl. No. 12/155,897.
Office Action mailed Oct. 12, 2011, in U.S. Appl. No. 12/155,897.
Office Action mailed Oct. 22, 2009, in co-pending U.S. Appl. No. 12/155,897.
Smith et al,. "Cardiovascular Safety of Degarelix: Results From a 12-Month, Comparative, Randomized, Open Label, Parallel Group Phase III Trial in Patients With Prostate Cancer," 184 The Journal of Urology 2313-2319 (2010).
Smith, M.R. et al., "Gonadotropin-Releasing Hormone Blockers and Cardiovascular Disease Risk: Analysis of Prospective Clinical Trials of Degarelix," 186 The Journal of Urology 1835-1842 (2011).
Sorbera et al., "Degarelix Acetate", GnRH Antagonist Prostate Cancer Therapy; Drugs of the Future 2006, vol. 31, No. 9, pp. 755-766.
Steinberg, et al., "Degarelix: A Gonadotropin-Releasing Hormone Antagonist for the Management of Prostate Cancer," Clinical Therapeutics, vol. 31, pp. 2312-2331.
Van Poppel, "Evaluation of degarelix in the management of prostate cancer," Cancer Management and Research, vol. 2, pp. 39-52, 2010.
Wolff, et al., "Cumulative analysis from six comparative randomised clinical trials of degarelix versus luteinising hormone-releasing hormone (LHRH) agonists: Better PSA-progressionfree survival confirmed in trials an everyday practice," (2012).

* cited by examiner

METHOD OF TREATING METASTATIC STAGE PROSTATE CANCER

This application claims the benefit of priority of U.S. Provisional Patent Application No. 61/147,956, filed Jan. 28, 2009, European Patent Application No. 08250703.9 filed Feb. 29, 2008, and U.S. Provisional Patent Application No. 61/027,741, filed Feb. 11, 2008, the entire contents of all of which are incorporated by reference.

Prostate cancer is a leading cause of morbidity and mortality for men in the industrialized world, accounting for about 9% of cancer-related deaths in men. Prostate cancer is the second leading cause of cancer death in American men, behind only lung cancer. The American Cancer Society has estimated that 27,050 men in the United States died of prostate cancer in 2007. In Europe, prostate cancer is the third most common cause of death from cancer in men in Europe, with 87,400 deaths estimated in 2006 (see Ferlay et al. (2007) *Ann. Oncol.*; 18:581-92; Lukka et al. (2006) *Curr. Oncol.*; 13:81-93.).

More than 9 out of 10 prostate cancers are found in the localized and locally advanced stages. When compared to men of the same age and race who do not have cancer (relative survival), the 5-year relative survival rate for the men who are diagnosed as having localized and locally advanced stage cancer is nearly 100%. However, the 5-year relative survival rate for men with metastatic stage prostate cancer that has already spread to distant parts of the body at the time of diagnosis is only about 32%. (see Cancer Trends Progress Report (http://progress report.cancer.gov; SEER Program and the National Center for Health Statistics; http://seer.cancer.gov/). In this last metastatic stage, the accelerated drop in survival rate is accompanied by symptoms including pain (e.g. bone pain), weight loss and fatigue. Therefore, treatments which lead to a reduction or staying of bone metastatic tumor cell growth would not only provide an increased life expectancy, which may be up to about 3 years or more, but would also provide an improved quality of life (QoL) as these symptoms are ameliorated.

As the majority of prostate cancers are dependent on testosterone for growth, the current medical management of advanced prostate cancer involves hormone-based treatments, such as androgen deprivation, which may be achieved by bilateral orchiectomy or by administration of gonadotrophin releasing hormone (GnRH) receptor agonists. Removal of the testes (castration) was for many years the standard method of preventing the secretion of male hormones by the gonads as a means for reducing growth of prostate cancers. More recently, secretion of male hormones has been perturbed by chemical means by interfering with production of luteinizing hormone (LH), which regulates the synthesis of androgens. Evidence from randomized studies strongly suggests that early endocrine therapy in non-metastatic, locally advanced disease with or without lymph node metastases is associated with a survival benefit (see Granfors et al. (1998) *J. Urol.* 159:2030-34; Messing et al. (1999) *N. Eng. J. Med.* 341:1781-88; and (1997) *Br. J. Urol.* 79:235-46).

Gonadotrophin releasing hormone (GnRH) is a natural hormone produced by the hypothalamus that interacts with a receptor in the pituitary to stimulate production of luteinizing hormone (LH). To decrease LH production, agonists of the GnRH receptor (GnRH-R), such as leuprolide and goserelin, have been developed. GnRH-R agonists initially act to stimulate LH release and only after prolonged treatment act to desensitize GnRH-R such that LH is no longer produced. The initial stimulation of LH production by the agonist leads to an initial surge in the production of male sex hormones such that the initial response to agonist therapy is aggravation, rather than amelioration, of the patient's condition (e.g., tumor growth may increase). This phenomenon, known as the "testosterone surge" or "flare reaction," can last for as long as two to four weeks. Additionally, each successive administration of the agonist can cause an additional small LH surge (known as the "acute-on chronic" phenomenon) that can further worsen the condition. The testosterone surge stimulates prostate cancer and can lead to a worsening of current symptoms or appearance of new symptoms such as spinal cord compression, bone pain and urethral obstruction (Thompson et al. (1990) *J. Urol.* 140:1479-80; Boccon-Gibod et al. (1986) *Eur. Urol.* 12:400-402). The relative efficacy and safety (including adverse side effects) of the GnRH agonist therapy leuprolide (also leuprorelin or LUPRON DEPOT) is known in the art (see e.g., Persad (2002) *Int. J. Clin. Pract.* 56:389-96; Wilson et al. (2007) *Expert Opin. Invest. Drugs* 16:1851-63; and Berges et al. (2006) *Curr. Med. Res. Opin.* 22:649-55). One approach that has been taken to avoid the testosterone surge (flare reaction) has been to combine administration of a GnRH-R agonist with an antiandrogen, such as flutamide, known as total androgen ablation therapy (AAT). Hormonal therapy with a GnRH-R agonist in combination with an antiandrogen has been used as a pre-treatment prior to radical prostatectomy known as adjuvant therapy. The use of antiandrogens, however, is associated with serious hepatic and gastrointestinal side effects.

The drawbacks associated with antiandrogens have led to the development of antagonists of the gonadotrophin releasing hormone receptor (GnRH-R), to overcome the "testosterone surge" or "flare reaction" associated with GnRH agonists. GnRH antagonists competitively bind to and block the GnRH receptors and cause a rapid decrease of LH and Follicle Stimulating Hormone (FSH) secretion, thereby reducing testosterone production with no initial stimulation/surge. However, GnRH antagonist peptides are frequently associated with the occurrence of histamine-releasing activity. This histamine-releasing activity represents a serious obstacle to the clinical use of such antagonists because histamine release results in adverse side effects such as edema and itching.

The search for improved GnRH antagonists has resulted in the making of Antide, Cetrorelix and Antarelix (U.S. Pat. No. 5,516,887). GnRH antagonists having such significantly modified or unnatural amino acids in the 5- and 6-positions exhibit good biological potency, and those built upon Aph are generally considered to be particularly potent. One that is especially useful is Azaline B. U.S. Pat. No. 5,506,207 also discloses biopotent GnRH antagonists with acylated, amino-substituted phenylalanine side chains of residues in the 5- and 6-positions; one such decapeptide is Acyline.

Despite the attractive properties of this group of GnRH antagonists, adverse effects have been observed. The relative efficacy and safety (including adverse side effects) of the GnRH antagonist abarelix (PLENAXIS) has been reported (see, e.g., Mongiat-Artus et al. (2004) *Expert Opin. Pharmacother.* 5:2171-9; and Debruyne et al. (2006) *Future Oncol.* 2:677-96). As such, the search has continued for still further improved GnRH antagonists, particularly those which combine long duration of biological action, and improved safety profile.

These desirable features have been addressed in several issued patents and patent applications, relating to a GnRH antagonist, degarelix, for treatment of prostate cancer (see, e.g., EP 1003774, U.S. Pat. No. 5,925,730, U.S. Pat. No. 6,214,798, EP 02749000.2 and U.S. Ser. No. 12/155,897 and EP 08250703.9, the contents of which are hereby incorporated in their entirety). In addition, U.S. Ser. No. 61/027,742 discloses the results of a long term evaluation in a multicentre randomized clinical study which demonstrate that degarelix is well-tolerated without evidence of systemic allergic reactions. Degarelix treatment also resulted in fast, profound and sustained suppression of testosterone (T) without T surge, as well as good efficacy and safety findings.

However, although continued investigations have allowed progress in the general prevention and treatment of prostate and other cancers, there has been little or no focus on addressing patients suffering at the late metastatic stage of cancer.

SUMMARY OF THE INVENTION

The invention is based, in part, upon the surprising finding that administration of the GnRH antagonist degarelix to patients with metastatic stage prostate cancer, and/or to patients having PSA levels of 50 ng/mL or greater, provides a remarkable, and long term, reduction of serum alkaline phosphatase (S-ALP) that is indicative of better control of (e.g. skeletal) metastases (see Example 1, FIGS. 1-4, Table 2). The results further evidence that administration of degarelix delays or prevents progression from localized or locally advanced stage prostate cancer to metastatic stage. Further, the results evidence that administration of degarelix to these patients is associated with a delay in progression to hormone refractory stage. Notably, this remarkable long term reduction of S-ALP is not shown following administration of the GnRH agonist leuprolide.

In a first aspect, the invention provides a method of treating metastatic stage prostate cancer in a subject. The method includes the initial step of identifying a suitable subject with metastatic stage prostate cancer, and then administering an initial dose of degarelix of 160 to 320 mg to the subject. The subject is then administered a maintenance dose of degarelix of 60 to 160 mg once every 20 to 36 days thereafter. The method thereby treats the metastatic stage prostate cancer in the subject. In a particular aspect, the invention provides a method of treating metastatic stage prostate cancer in a subject, which includes the initial step of identifying a suitable subject with metastatic stage prostate cancer, and then administering an initial dose of degarelix of about 240 mg to the subject. The subject is then administered a maintenance dose of degarelix of 60 to 160 mg once every 20 to 36 days thereafter. The method thereby treats the metastatic stage prostate cancer in the subject.

In certain embodiments of the methods of the invention, the subject to be treated is identified by testing the serum alkaline phosphatase (S-ALP) level of a potential subject and then selecting the subject for treatment if the subject's baseline S-ALP level is 150 IU/L or greater, e.g. 160 IU/L or greater. In further embodiments, the subject to be treated is identified by testing the serum alkaline phosphatase (S-ALP) level of a potential subject and then selecting the subject for treatment if the subject's baseline S-ALP level is 200 IU/L or greater. In still further embodiments, the subject to be treated is identified by testing the serum alkaline phosphatase (S-ALP) level of a potential subject and then selecting the subject for treatment if the subject's baseline S-ALP level is 300 IU/L or greater.

In further embodiments of the methods of the invention, the subject to be treated is identified by testing the hemoglobin (Hb) level of a potential subject and then selecting the subject for treatment if the subject's Hb level is 130 g/L or less. In still further embodiments, the subject to be treated is identified by testing the prostate-specific antigen (PSA) level of a potential subject and then selecting the subject for treatment if the subject's PSA level is greater than or equal to 50 ng/mL. In particular embodiments, the treated subject's S-ALP is reduced by at least 60 IU/L from the baseline level between day 112 and day 364 of treatment.

In further embodiments of the methods of the invention, the treated subject's serum alkaline phosphatase (S-ALP) is reduced by at least 50 IU/L from the baseline level between day 60 and day 364 of treatment. In other embodiments, the treated subject's S-ALP is reduced by at least 50 IU/L from the baseline level between day 364 and day 450 of treatment. In further embodiments, the treated subject's S-ALP is reduced by at least 90 IU/L from the baseline level between day 112 and day 364 of treatment. In still further embodiments, the treated subject's S-ALP is reduced by at least 160 IU/L from the baseline level between day 112 and day 364 of treatment.

In further embodiments of the methods of the invention, the treated subject has at least a 95% likelihood of having a therapeutically low serum testosterone level of less than or equal to 0.5 ng/mL by day 28 of treatment. In particular embodiments, the treated subject has at least a 95% likelihood of maintaining a therapeutically low serum testosterone level of less than or equal to 0.5 ng/mL from day 28 to day 365 of treatment.

In still further embodiments of the methods of the invention, the treated subject has at least a 60% decrease in the level of prostate-specific antigen (PSA) by day 14 of treatment. In certain embodiments, the treated subject has at least a 75% decrease in the level of PSA by day 28 of treatment. In further embodiments, the treated subject has at least an 80% likelihood of maintaining a prostate-specific antigen (PSA) level of less than 5 ng/mL during treatment.

In another aspect, the invention provides a method of treating prostate cancer by first testing the prostate-specific antigen (PSA) of a potential subject, and then selecting the potential subject for treatment if the subject's PSA level is greater than or equal to 50 ng/mL. The method further includes the steps of administering an initial dose of degarelix of 160 to 320 mg to the subject thus identified, and then administering a maintenance dose of degarelix of 60 to 160 mg to the subject once every 20 to 36 days thereafter, so as to treat the prostate cancer in the subject.

In certain embodiments of the methods of the invention, the subject to be treated is further identified by testing the serum alkaline phosphatase (S-ALP) level of a potential subject and then selecting the subject for treatment if the subject's baseline S-ALP level is 150 IU/L or greater, e.g. 160 IU/L or greater. In certain embodiments, the treated subject's S-ALP is reduced by at least 60 IU/L from the baseline level between day 112 and day 364 of treatment. In further embodiments, the subject to be treated is further identified by testing the hemoglobin (Hb) level of the potential subject and then selecting the subject for treatment if the subject's Hb level is 130 g/L or less.

In another aspect, the invention provides methods of using degarelix for the treatment of metastatic stage prostate cancer in a subject. The methods of use of degarelix include an initial step of identifying a suitable subject with metastatic stage prostate cancer. The suitable subject thus identified is then administered an initial dose of degarelix of 160 to 320 mg, followed by maintenance doses of 60 to 160 mg of degarelix once every 20 to 36 days thereafter, thereby using degarelix for the treatment of metastatic stage prostate cancer.

In certain embodiments of the methods of use of degarelix, the subject with metastatic stage prostate cancer is identified by testing the serum alkaline phosphatase (S-ALP) level of a potential subject and then selecting the subject for treatment if the subject's baseline S-ALP level is 150 IU/L or greater, e.g. 160 IU/L or greater. In further embodiments, the subject with metastatic stage prostate cancer is identified by testing the serum alkaline phosphatase (S-ALP) level of a potential subject and then selecting the subject for treatment if the subject's baseline S-ALP level is 200 IU/L or greater. In still further embodiments, the subject with metastatic stage prostate cancer is identified by testing the serum alkaline phosphatase (S-ALP) level of a potential subject and then selecting the subject for treatment if the subject's baseline S-ALP level is 300 IU/L or greater. In certain embodiments, the subject with metastatic stage prostate cancer is identified by testing the hemoglobin (Hb) level of a potential subject and then selecting the subject for treatment if the subject's Hb level is 130 g/L or less. In other embodiments, the subject with metastatic stage prostate cancer is identified by testing the prostate-specific antigen (PSA) level of a potential subject and then selecting the subject for treatment if the subject's PSA level is greater than or equal to 50 ng/mL.

In another aspect, the invention provides methods of using degarelix to prevent or delay the progression of localized or locally advanced prostate cancer to metastatic stage prostate cancer in a subject. The methods of use of degarelix to prevent or delay the progression of localized or locally advanced prostate cancer include the initial step of identifying a suitable subject with localized or locally advanced prostate cancer. The suitable subject thus identified is then administered an initial dose of degarelix of 160 to 320 mg, followed by maintenance doses of 60 to 160 mg of degarelix once every 20 to 36 days thereafter. This method of use of degarelix thereby prevents or delays the progression of localized or locally advanced prostate cancer to metastatic stage prostate cancer in the subject.

In certain embodiments of the methods of use of degarelix to prevent or delay metastatic stage prostate cancer, the subject with localized or locally advanced prostate cancer is identified by testing the prostate-specific antigen (PSA) level of a potential subject and then selecting the subject for preventive or delaying treatment if the subject's PSA is 10-50 ng/mL. In further embodiments, the subject with localized or locally advanced prostate cancer is identified by testing the prostate-specific antigen (PSA) level of a potential subject and then selecting the subject for preventive or delaying treatment if the subject's PSA is 20-50 ng/mL. In further embodiments, the subject with localized or locally advanced prostate cancer is identified by testing the serum alkaline phosphatase (S-ALP) level of between 44 and 147 IU/L. In still further embodiments, the subject with localized or locally advanced prostate cancer is identified by testing the serum alkaline phosphatase (S-ALP) level of a potential subject and then selecting the subject for preventive or delaying treatment if the subject's baseline S-ALP level is less than about 160 IU/L. In certain embodiments, the subject with localized or locally advanced prostate cancer is identified by testing the serum alkaline phosphatase (S-ALP) level of a potential subject and then selecting the subject for preventive or delaying treatment if the subject's baseline S-ALP level is, for example 44 to 147 IU/L and/or between 50 and 160 IU/L.

In a further aspect, the invention provides a composition (e.g. a pharmaceutical composition, a medicament) comprising degarelix for the treatment of metastatic stage prostate cancer in a subject.

As used herein, the term metastasis refers to a secondary metastatic growth of a malignant tumor that forms when cancer has spread from an original site to more remote or distant parts of the body, for example the lymph nodes, bone, and/or other organs such as the brain or liver. Thus, the term "metastatic" or "metastatic stage prostate cancer" refers to a cancer that has spread to distant organs from the original tumour site, e.g., the prostate gland.

Herein, "treatment of metastatic stage prostate cancer" and associated methods of "treating metastatic stage prostate cancer" include treatments and associated methods to reduce the amount of cancerous tissue, e.g. by reducing the number and/or size of metastatic lesions (tumors), such as metastatic lesions in the bone, brain, liver and/or lymph nodes. As used herein, the "treatment of metastatic stage prostate cancer" and associated methods of "treating metastatic stage prostate cancer" refer particularly to treatments, and associated methods, to reduce skeletal metastases (metastatic lesions identified in the skeleton, e.g., by bone scan or other imaging technique).

Herein, "treatment of metastatic stage prostate cancer" and associated methods of "treating metastatic stage prostate cancer" further Include treatments and associated methods to reduce and/or ameliorate one or more symptoms associated with metastatic stage prostate cancer, e.g. treatment to ameliorate and/or reduce the symptoms of urinary disorders (e.g. obstruction, weak or interrupted urination, frequent urination, inability to urinate, pain while urinating, blood in the urine), treatment to reduce and/or ameliorate bone pain (e.g. in the lower back, hips or thighs), and/or treatment to reduce and/or ameliorate weight loss, fatigue.

In another aspect of the invention, there is provided a composition comprising degarelix for the treatment of metastatic stage prostate cancer in a subject to reduce the number and/or size of metastatic lesions and/or to reduce and/or ameliorate one or more symptoms associated with metastatic stage prostate cancer.

The terms "prevention of metastatic stage prostate cancer" and associated methods of "preventing metastatic stage prostate cancer" further include treatments, and associated methods that prevent the onset of metastatic activity or that maintains the level of metastatic activity (e.g. at the level known at start of medication, i.e. baseline), or that reduce and/or delay the return of metastatic activity (e.g. as measured by S-ALP), in a subject being treated for prostate cancer who is at the locally advanced stage. The expression "the level of metastatic activity" in this context refers to the size and/or number of metastatic tumors in the subject, and not the rate of metastasis in the subject per se.

Accordingly, the invention includes treatments and associated methods to delay or prevent progression of the disease and/or to bring on or enhance regression or remission of the disease. For example, the term "prevention of metastatic stage prostate cancer" and associated "methods of preventing metastatic stage prostate cancer" include treatments and associated methods to prolong the life and/or increase the quality of life (QoL) of the patient.

Herein the terms "treatment of metastatic [stage] prostate cancer" and associated "methods of treating metastatic [stage] prostate cancer", or, "treatment of prostate cancer" and associated "methods of treating prostate cancer" may also include treatments and associated methods that delay or prevent onset of the hormone-refractory disease stage.

Thus, according to the present invention in yet another aspect, there is provided a composition comprising degarelix for the treatment of prostate cancer in a subject and associated methods of treatment that reduce the likelihood of, and/or delay, the return of metastatic tumor activity, and/or that delay or prevent progression of the disease, and/or bring on or increase regression or remission of the disease, and/or prolong the life and/or increase the quality of life (QoL) of the patient, and/or delay or prevent onset of the hormone-refractory disease stage.

The term "treatment of prostate cancer" and associated "methods of treating prostate cancer" also include treatment and associated methods to cure the prostate cancer.

Applicants now disclose that the administration of the GnRH antagonist degarelix to patients with metastatic stage prostate cancer and/or patients having PSA level of about 50 ng/mL or greater, provides a remarkable, and long term, reduction of serum alkaline phosphatase (S-ALP) (See FIGS. 1 and 4, Table 2). Not only is the reduction in the S-ALP value significant, but more importantly, the steady and maintained low levels of S-ALP levels over a long term period (See FIG. 3), is indicative of better control of (e.g. bone) metastases. This remarkable long term reduction of S-ALP is not shown following administration of the GnRH agonist leuprolide.

The remarkable long term reduction of S-ALP following administration of the GnRH antagonist degarelix to patients with metastatic stage prostate cancer and/or patients having PSA level of about 50 ng/mL or greater also provides evidence that administration of degarelix to these patients provides a delay in progression of the cancer to the hormone refractory stage.

The subject may have a baseline serum alkaline phosphatase (S-ALP) level (that is, a S-ALP level prior to treatment i.e. prior to administration of the initial dose of testosterone) of about 150 IU/L or greater, e.g., a baseline serum alkaline phosphatase (S-ALP) level of about 160 IU/L or greater, e.g., a baseline serum alkaline phosphatase (S-ALP) level of about 200 IU/L or greater, or even a baseline serum alkaline phosphatase (S-ALP) level of about 300 IU/L or greater (See Table 2).

In further embodiments, the degarelix composition provides a reduction below the baseline (or alternatively articulated, a negative change from baseline) of serum alkaline phosphatase (S-ALP) level of at least about 50 IU/L below the baseline (S-ALP) for a period between about 60 and 364 days after administration of the initial dose of degarelix, and/or, at least about 90 IU/L below the baseline level for a period between 112 and 364 days after administration of the initial dose of degarelix. (See Table 2, FIGS. 1-3). In certain embodiments, reduction in serum alkaline phosphatase (S-ALP) level of at least about 50 IU/L below the baseline level extends for a period beyond 364 days (depending on continuation of therapy/maintenance doses, see below).

In still further embodiments, the subject to whom the treatment is administered has a hemoglobin (Hb) level of about 130 g/L or less. Baseline S-ALP levels were particularly elevated in the subgroup of patients with metastatic disease and Hb<130 g/L; for example a baseline serum alkaline phosphatase (S-ALP) level of 300 IU/L or greater was found in a population of patients having a Hb<130 g/L (See Table 2). In particular embodiments, the subject with the aforementioned depressed Hb level also shows a reduction (alternatively, a negative change from baseline) of serum alkaline phosphatase (S-ALP) level of at least 160 IU/L below the baseline level for a period between 112 and 364 days after administration of the initial dose of degarelix (See FIG. 2). Bone metastases affect bone marrow and a patient with bone metastasis may become anemic; thus lower than normal Hb in patients with bone metastasis is indicative of greater degree of metastasis (more serious disease). As described in further detail herein, the invention provides a surprisingly long term and effective suppression of S-ALP by degarelix in this subpopulation of patients with lower than normal Hb levels.

According to the present invention in a further aspect, there is provided a composition comprising degarelix for the treatment of prostate cancer in a subject having a prostate specific androgen (PSA) level of greater than or equal to 50 ng/mL (See FIG. 4). In particular embodiments, the prostate cancer to be treated is metastatic prostate cancer.

In aspects of the invention, the composition may be for administration of degarelix at an initial dose of 160 to 320 mg; and at a maintenance dose of 60 to 160 mg, once every 20 to 36 days thereafter, for example for administration at an initial dose of degarelix of about 240 mg; and at a maintenance dose of about 80 mg degarelix once every approximately 28 days of treatment.

In certain embodiments, the composition of degarelix is for treatment wherein the subject has at least a 95% likelihood of maintaining a therapeutically low serum testosterone level of less than or equal to 0.5 ng/mL by day 28 of treatment, for example wherein the subject has at least a 95% likelihood of maintaining a therapeutically low serum testosterone level of less than or equal to 0.5 ng/mL from day 28 to day 364 of treatment. (See, e.g., FIGS. 7-8).

In still further embodiments, the composition of degarelix is for treatment of metastatic prostate cancer and provides a 60% decrease in PSA by day 14 of treatment. In still further embodiments, the composition (or medicament) of degarelix provides at least a 60% decrease, e.g., at least a 75% decrease, in prostate specific antigen (PSA) by day 28 of treatment. (See, e.g., FIG. 9).

In further embodiments, the composition of degarelix is for treatment with at least an 80%; for e.g., a 95% likelihood, of maintaining a prostate specific antigen (PSA) level of less than 5 ng/mL during treatment.

According to another aspect of the invention, there is provided a method of treating metastatic prostate cancer in a subject comprising administering an initial dose of 160-320 mg of degarelix to the subject; and administering a maintenance dose of 60-160 mg of degarelix to the subject once every 20-36 days thereafter; for example, administering an initial dose of about 240 mg of degarelix to the subject; and administering a maintenance dose of about 80 mg of degarelix to the subject once every approximately 28 days thereafter.

DETAILED DESCRIPTION OF THE INVENTION

Terms and Definitions

Figure 1:
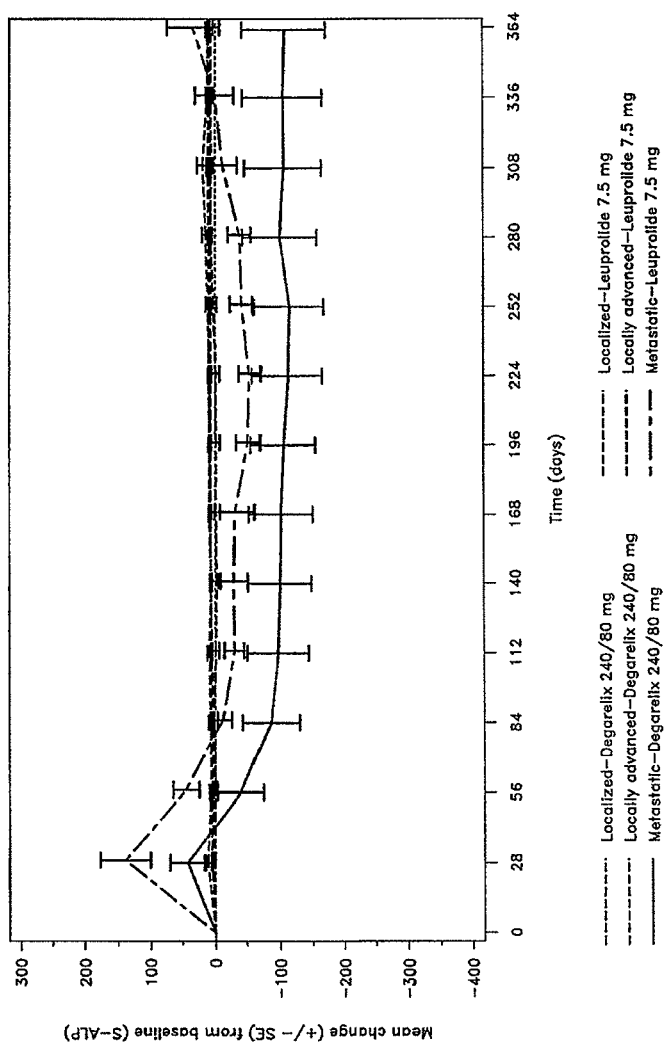
FIG. 1 is a graphical representation comparing the mean change in baseline S-ALP levels versus time, for the local (localized), locally advanced and metastatic populations, using degarelix (240/80 mg) and leuprolide (7.5 mg) treatments.

Particular aspects of the invention are described in greater detail below. The terminologies and definitions as used in the present application as clarified herein are intended to represent the meaning of the applicants in their disclosure of the invention. The patent and scientific literature referred to herein are hereby incorporated by reference in their entireties.

The singular forms "a," "an," and "the" include plural reference unless the context clearly dictates otherwise.

The terms "approximately" and "about" mean to be nearly the same as a referenced number or value. As used herein, the terms "approximately" and "about" should be generally understood to encompass ±10% of a specified amount, frequency or value. The term "CI" refers to a statistical confidence interval. With regard to specific values of, e.g., serum alkaline phosphatase (S-ALP), prostate specific antigen (PSA), hemoglobin (Hb), testosterone, luteinizing hormone (LH), and follicle stimulating hormone (FSH), it should be understood that specific values described herein for subject populations (e.g., the subjects of clinical study CS21, described below) represent average (i.e., mean values), unless otherwise noted as, e.g., median values. Accordingly, aspects of the invention requiring a particular value of S-ALP, PSA, and/or Hb level in a subject are substantially supported herein by population data in which the relevant value is assessed to be a meaningful delimitation of the subject population.

In general, the invention provides use of a composition comprising degarelix GnRH antagonist for treating metastatic prostate cancer in a subject, and related methods of treatment. The disclosure of the invention has been exemplified by data obtained from clinical studies, in particular, the CS21 study on Degarelix (EP application No. 08250703.9, and U.S. provisional application No. 61/027,741). A review of the basic methods for conducting and analyzing the type of controlled clinical studies described herein, including analyses of safety, efficacy and selective advantages to certain patient subpopulations, is available (see Spilker (1991) Guide to Clinical Trials Raven Press, New York; and Spilker (1996) Quality of Life and Pharmacoeconomics in Clinical Trials Lippincott—Raven Publishers New York).

The term "prostate cancer" refers to any cancer of the prostate gland in which cells of the prostate mutate and begin to multiply out of control. The extent to which prostate cancer has progressed in a patient is assessed taking into account clinical and histopathological information. The stage of cancer is classified based on tumour size (T), whether there is lymph node involvement (N), the presence of metastasis (M), and the tumour grading (G). A tumour classed as T1 is confined to the prostate gland and too small to be felt by digital rectal examination. T1 further includes T1a (fewer than 5% cancerous cells in tissue sample) and T1b (more than 5%) subdivisions. T1c indicates the patient has an elevated Prostrate Specific Antigen (PSA; see definition later). If the tumour is large enough to be felt during a digital rectal examination, it is classified as T2. T2a means only one side of the prostate gland (left or right) is involved; T2b means both sides have a tumour(s). T2 is commonly termed "localized cancer". If the cancer is T3, it has spread to the connected tissue near the prostate (T3a) or the seminal vesicles (T3b). T4 indicates cancer spread to tissue next to the prostate, for example the bladder sphincter, rectum or pelvis wall. The prostate cancer may also spread into the regional lymph nodes of the pelvis and this is assessed as N1 stage of prostate cancer. These stages of T3, T4 and N1 are collectively termed "locally advanced" or regional cancer. If the cancer has spread to distant sites, such as the bone, it is said to be "metastasized" or at the M1 stage. Prostate cancer that has spread to distant lymph nodes is categorized as M1a while that which has spread to bone is M1b and that which has spread to organs such as liver or brain is assessed as M1c. Left untreated, prostate cancer almost universally metastasizes to bone.

Terms as used in this application, such as "bone metastasis", "skeletal metastases", "bone lesions", "metastatic lesions" refer to the metastatic stage and may be used interchangeably. Pain (e.g. bone pain), weight loss and fatigue often accompany the M1 stage. Survival rate also drops significantly for subjects with metastatic prostate cancer. Treatments which lead to a reduction of bone metastasis imply not only an improved quality of life (QoL), such as decreased pain, bone loss, but more significantly, an increased life expectancy, up to about 3 years or more. At a certain point, however, metastatic patients may fail to respond to hormone-based treatments; this is known as the "hormone-refractory" disease stage. According to this terminology, and as adopted in this application, the term "treatment of metastatic prostate cancer" includes treatment of a subject who is classified as M1a, M1b or M1c, and/or N1.

In general, androgen deprivation induces a remission in 80 to 90 percent of men with advanced prostate cancer, and results in a median progression free survival of 12 to 33 months. At that time, an androgen independent phenotype usually emerges. Hormone refractory prostate cancer (which may also be referred to as hormone-resistant prostate cancer or hormone independent prostate cancer) is broadly defined herein as prostate cancer wherein the patient's blood PSA is rising despite having a castrate level of testosterone (T less than 20 ng/dL) caused by hormone blockade therapy. [Murphy D. (1993) *Cancer* 72: 3888-3895; Hellerstedt B A and Pienta K J (2002) *CA Cancer J. Clin.* 52: 154-179.]

Alkaline phosphatase (ALP) is a hydrolase enzyme responsible for removing phosphate groups from many types of molecules, including nucleotides, proteins, and alkaloids. In humans, ALP is present in all tissues throughout the entire body, but is particularly concentrated in liver, bile duct, kidney, bone and the placenta. Its concentration level may be used as a diagnostic tool; abnormally elevated levels (hyperphosphatasemia) may indicate several disorders. These include liver disease, bone disease, skeletal involvement of other primary diseases such as malignant tumours, osteomalacia, renal disease (secondary hypothyroidism), and primary hypothyroidism. On the other hand, abnormally lowered levels of ALP (hypophosphatasemia) may indicate other disorders, such as severe anemia in men, or achondroplasia, cretinism, or severe enteritis in children. In general, levels of ALP present in a subject's serum (S-ALP levels) are used in conjunction with the treatment methods and compositions described herein.

S-ALP testing is well known in the art (Chernecky C C, Berger B J (2008), *Laboratory Tests and Diagnostic Procedures*, 5th ed., WB Saunders & Company, Philadelphia). It is generally used as a test of liver function, but is also known as an indicator for metastatic lesions in the bone for different malignancies (breast, prostate and colon). In metastatic prostate cancer, baseline S-ALP levels (or alternatively, "ALP levels") are consistently higher than in localized or locally advanced disease reflecting bone lesions. As disclosed in the present invention, the subject may have a baseline serum alkaline phosphatase (S-ALP) level (that is, a S-ALP level prior to treatment i.e. prior to administration of the initial dose of testosterone) of 160 IU/L or greater, for example a baseline serum alkaline phosphatase (S-ALP) level of 200 IU/L or greater. A decrease in baseline S-ALP levels in a treated subject suffering from metastatic prostate cancer therefore demonstrates a positive response to the treatment in certain circumstances.

One of the most important techniques for diagnosis of prostate cancer is blood testing; specifically, in the measurement of prostate-specific antigen (PSA) levels in the blood. The term "prostate-specific antigen" or "PSA" refers to a protein produced by cells of the prostate gland that is present in small quantities in the serum of normal men, but is often elevated in the presence of prostate cancer and in other prostate disorders. A blood test to measure PSA is the most effective test currently available for the early detection of prostate cancer. Levels of PSA, which are higher than normal, are associated with both localized and metastatic prostate cancer. According to the present invention, the subjects with localized or metastatic stage prostate cancer have a prostate specific androgen (PSA) level of greater than or equal to 50 ng/mL.

Degarelix and Related Pharmaceutical Formulations

Degarelix is a potent GnRH antagonist that is an analog of the GnRH decapeptide (pGlu-His-Trp-Ser-Tyr-Gly-Leu-Arg-Pro-Gly-NH$_2$) incorporating p-ureido-phenylalanines at positions 5 and 6 (Jiang et al. (2001) *J. Med. Chem.* 44:453-67). It is indicated for treatment of patients with prostate cancer in whom androgen deprivation is warranted (including patients with rising PSA levels after having already undergone prostatectomy or radiotherapy).

Degarelix is a selective GnRH receptor antagonist (blocker) that competitively and reversibly binds to the pituitary GnRH receptors, thereby rapidly reducing the release of gonadotrophins and consequently testosterone (T). Prostate cancer is sensitive to testosterone deprivation, a mainstay principle in the treatment of hormone-sensitive prostate cancer. Unlike GnRH agonists, GnRH receptor blockers do not induce a luteinizing hormone (LH) surge with subsequent testosterone surge/tumor stimulation and potential symptomatic flare after the initiation of treatment.

The active ingredient degarelix is a synthetic linear decapeptide amide containing seven unnatural amino acids, five of which are D-amino acids. The drug substance is an acetate salt, but the active moiety of the substance is degarelix as the free base. The acetate salt of degarelix is a white to off-white amorphous powder of low density as obtained after lyophilisation. The chemical name is D-Alaninamide, N-acetyl-3-(2-naphthalenyl)-D-alanyl-4-chloro-D-phenylalanyl-3-(3-pyridinyl)-D-alanyl-L-seryl-4-[[[(4S)-hexahydro-2,6-dioxo-4-pyrimidinyl]carbonyl]amino]-L phenylalanyl-4-[(aminocarbonyl)amino]-D-phenylalanyl-L leucyl-N-6-(1-methylethyl)-L-lysyl-L-prolyl. It has an empirical formula of $C_{82}H_{103}N_{18}O_{16}Cl$ and a molecular weight of 1,632.3 Da. The chemical structure of degarelix has been previously shown (EP 1003774, U.S. Pat. No. 5,925,730, U.S. Pat. No. 6,214,798) and may be represented by the formula:

Ac-D-NaI-D-Cpa-D-PaI-Ser-Aph(Hor)-D-Aph(Cbm)-Leu-Lys(iPr)-Pro-D-Ala-NH$_2$.

Administration and Dosing

Degarelix may be formulated for administration subcutaneously (as opposed to intravenously), generally in the abdominal region, as described in further detail below. As with other drugs administered by subcutaneous injection, the injection site may vary periodically to adapt the treatment to injection site discomfort. In general, injections should be given in areas where the patient will not be exposed to pressure, e.g. not close to waistband or belt and not close to the ribs.

Administration of degarelix by subcutaneous or intramuscular injection works well, but daily injections are generally not acceptable and so a depot formulation of degarelix may be utilized as describe in further detail in WO 03/006049 and U.S. Pub. Nos. 20050245455 and 20040038903. Briefly, subcutaneous administration of degarelix may be conducted using a depot technology in which the peptide is released from a biodegradable polymer matrix over a period of (typically) one to three months. Degarelix (and related GnRH antagonist peptides) have a high affinity for the GnRH receptor and are much more soluble in water than other GnRH analogues. Degarelix and these related GnRH antagonists are capable of forming a gel after subcutaneous injection, and this gel can act as a depot from which the peptide is released over a period of weeks or even months.

A key variable for formation of an effective degarelix depot is the concentration of the solution in combination with the amount of substance administered per se. The concentration must be within a functional range. If the formulation is too dilute then no depot is formed and the long duration of action is lost, regardless of the amount of drug substance given. If the formulation is too concentrated then gel formation will occur before the drug can be administered. Effective depot-forming formulations of degarelix generally have a concentration of not less than 5 mg/mL degarelix, e.g. 5 to 40 mg/mL of degarelix.

Thus, degarelix may be provided as a powder for reconstitution (with a solvent) as solution for injection (e.g., subcutaneous injection, e.g., to form a depot as described above). The powder may be provided as a lyophilisate containing degarelix (e.g. as acetate) and mannitol. A suitable solvent is water (e.g., water for injection, or WFI). For example, degarelix may be provided in a vial containing 120 mg degarelix (acetate) for reconstitution with 3 mL WFI such that each mL of solution contains about 40 mg degarelix. In another example, degarelix may be provided in a vial containing 80 mg degarelix (acetate). After reconstitution with about 4 mL (e.g., 4.2 mL) WFI, each mL solution contains about 20 mg degarelix.

According to the invention, there is provided a method of treating metastatic prostate cancer in a subject comprising administering an initial dose of 160-320 mg of degarelix to the subject; and administering a maintenance dose of 60-160 mg of degarelix to the subject once every 20-36 days thereafter; for example, administering an initial dose of about 240 mg of degarelix to the subject; and administering a maintenance dose of about 80 mg of degarelix to the subject once every approximately 28 days thereafter.

The composition may be for administration of degarelix at an initial dose of 160 to 320 mg; and at a maintenance dose of 60 to 160 mg, once every 20 to 36 days thereafter.

A preferred dosing regimen for treating adult males with prostate cancer is a single 240 mg starting dose of degarelix administered as two subcutaneous injections of 120 mg; and followed by monthly maintenance doses of 80 mg of degarelix administered as a single subcutaneous injection beginning approximately 28 days or one month after the initial starting dose.

For example, the dosing regimen for degarelix may be administered as an initial, starting dose of 240 mg administered as 2 injections of 3 mL of about 40 mg/mL degarelix formulation, followed by monthly maintenance doses of 80 mg administered as a single injection of 4 mL of about 20 mg/mL degarelix formulation. Alternatively, monthly maintenance doses of 160 mg may be utilized, e.g., by administering 4 mL of about 40 mg/mL degarelix every month.

The reconstituted solution should be a clear liquid, free of undissolved matter. A single dose of 240 mg degarelix, followed by a monthly maintenance dose of 80 mg, rapidly causes a decrease in the concentrations of the luteinizing hormone (LH), follicle stimulating hormone (FSH), and subsequently testosterone. The plasma concentration of dihydrotestosterone (DHT) decreases in a manner similar to that of testosterone.

Degarelix is effective in achieving and maintaining testosterone suppression well below medical castration level of 0.5 ng/mL. As described below in further detail, maintenance monthly dosing of 80 mg resulted in sustained testosterone suppression in 97% of patients for at least one year. In particular, the median testosterone level after one year of such treatment was 0.087 ng/mL.

The relevant pharmacokinetic parameters for degarelix evaluated in prostate cancer patients are summarized in Table 1, below.

TABLE 1

Degarelix pharmacokinetic parameters after subcutaneous administration of 240 mg at a concentration of 40 mg/mL

| Pharmacokinetic parameter | degarelix 240 mg |
|---|---|
| Cmax (ng/mL) | 53.4 |
| Tmax (days) | 1.4 |
| T½ (days) | 43 |
| AUC (day · ng/mL) | 1240 |

Median degarelix trough concentrations in the maintenance phase with 80 mg at a concentration of 20 mg/mL was 10.9 ng/mL.

Following subcutaneous administration of 240 mg degarelix (6 mL at a concentration of 40 mg/mL) to prostate cancer patients, degarelix is eliminated in a biphasic fashion, with a median terminal half-life of approximately 43 days.

The long half-life after subcutaneous administration is a consequence of a very slow release of degarelix from the depot formed at the injection site(s).

The pharmacokinetic behavior of the drug is strongly influenced by its concentration in the injection suspension.

The resulting distribution volume in healthy elderly men is approximately 1 L/kg. Plasma protein binding is estimated to be approximately 90%.

Degarelix is subject to common peptidic degradation during the passage of the hepato-biliary system and is mainly excreted as peptide fragments in the feces. No significant metabolites were detected in plasma samples after subcutaneous administration. In vitro studies have shown that degarelix is not a substrate for the human CYP450 (cytochrome P450) system. Therefore, clinically significant pharmacokinetic interactions with other drugs are unlikely to occur.

In healthy men, approximately 20% of a given dose of degarelix was renally excreted, suggesting that approximately 80% is excreted via the hepato-biliary system in humans. The clearance in healthy elderly men is 35-50 mL/hr/kg.

Adverse Events (Side Effects)

Degarelix has been found to be generally well tolerated in clinical trials. The most commonly observed adverse reactions during therapy were due to the expected physiological effects of testosterone suppression, mainly hot flushes and increased weight, and injection site related adverse events (injection site related side effects), mainly injection site pain and injection site erythema.

EXAMPLES

Example 1

S-ALP Levels in Prostate Cancer Patients Treated with Degarelix Versus Leuprolide Example 1 gives the results of the analyses of serum alkaline phosphatase (S-ALP) performed on patients undergoing treatment for prostrate cancer, using alternatively, degarelix (240/80 mg) and leuprolide (7.5 mg) treatments.

Methods:

Patients with histologically confirmed adenocarcinoma of the prostate (all stages), for whom androgen deprivation therapy was indicated were recruited. Baseline characteristics were well balanced between groups. Approximately half of patients had locally advanced (29.2%) or metastatic (20.5%) disease at baseline. A total of 610 patients (mean age 72 years, median testosterone was 39.3 ng/mL, and median PSA 19.0 ng/mL) were randomized to 1 of 3 dosing regimens: degarelix s.c. 240 mg for 1 month (initiation dose) followed by monthly maintenance doses of 160 mg (n=202) or 80 mg (n=207), or monthly intramuscular injections of leuprolide depot 7.5 mg (n=201). Patients receiving leuprolide could also receive bicalutamide for clinical flare protection.

S-ALP Analysis:

The S-ALP levels were measured in each patient at various time points, by taking a blood sample and analyzing for S-ALP. S-ALP levels were measured using a standardized colorimetric assay based on the p-nitrophenyl phosphate AMP buffer method. The normal range for S-ALP is 44-147 IU/L. The S-ALP values in non-metastatic patients serve as controls. An ANOVA analysis with treatment and day as factors and baseline value as covariate was used to determine between treatment differences at Day 364. A repeated measures analysis (incorporating all time points from Day 112) with treatment and day as factors and baseline value as covariate was used to assess between treatment differences from Day 112 to Day 364.

Results:

The results of S-ALP analyses for the degarelix 240/80 mg and leuprolide 7.5 mg groups in patients with advanced prostate cancer are presented in Table 2 and FIG. 1. In localized disease, S-ALP levels showed a small but gradual increase within normal range over the study period, irrespective of treatment group (leuprolide or degarelix). Similarly, in locally advanced disease, a small increase was observed by the end of the study in both treatment groups. Table 2 shows that baseline S-ALP levels are high in metastatic patients, and even more so in the patients with Hb<130 g/L, whichever the treatment. However, after initial peaks in both groups, as described earlier for hormonal treatments, S-ALP levels were suppressed below baseline with both degarelix 80 mg and leuprolide, though more significantly with degarelix. An initial increase (peak) in S-ALP is associated with increased activity in bone, and metastatic patients experience a surge in S-ALP at the initiation of all therapies having an effect on skeletal metastasis. This is a well described phenomenon and totally independent of testosterone surge.

Figure 3:
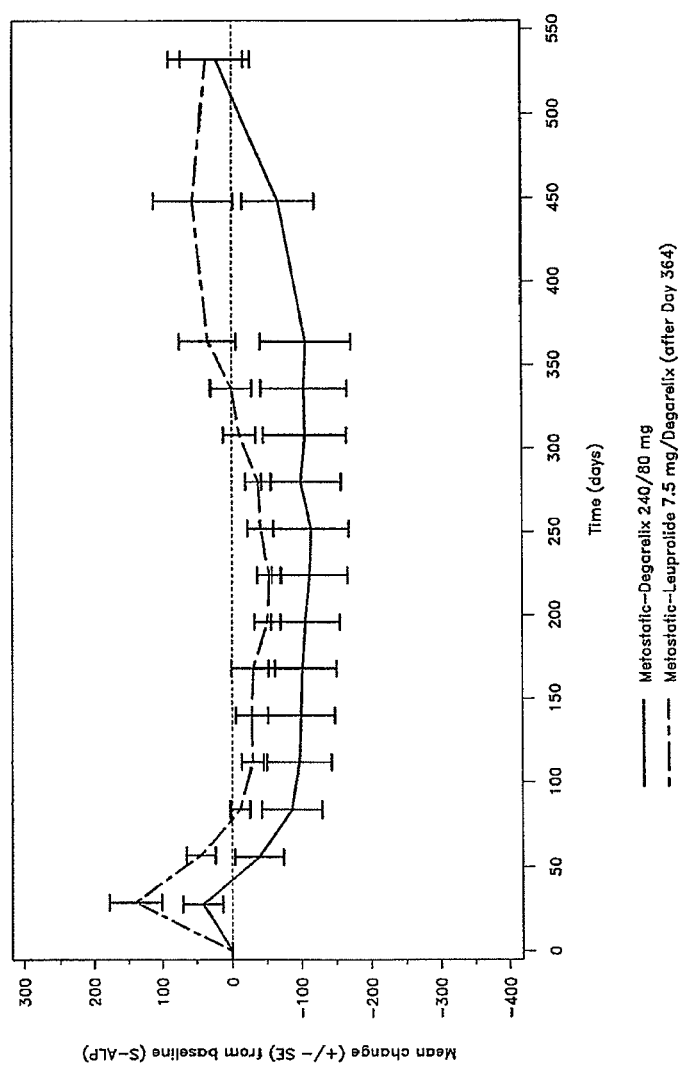
FIG. 3 is a graphical representation showing the mean change in baseline S-ALP values, versus time, using degarelix (240/80 mg) treatment as compared to leuprolide (7.5 mg) treatment that was "switched" to degarelix after day 364, which demonstrates the difference in time for the reduced baseline S-ALP values to return to baseline level.

FIG. 1 compares the mean change from baseline of S-ALP levels versus time for the localized, locally advanced, and metastatic populations, using degarelix (240/80 mg) and leuprolide (7.5 mg) treatments. These results clearly illustrate the long-term suppression of S-ALP using degarelix. A decrease in baseline S-ALP levels in a treated subject suffering from prostate cancer indicates a positive response to the treatment-, for example by reducing skeletal metastatic activity. Conversely, an increase in S-ALP indicates increased metastatic activity. FIG. 1 shows that degarelix treatment significantly reduces S-ALP (after an initial and expected surge) and then maintains the reduction for the duration of the study. Most significantly, S-ALP rises with leuprolide later in the study, indicating a return of metastatic activity. Such a return was not observed with degarelix until significantly later (FIG. 3). Thus, FIG. 1 indicates that degarelix is able to reduce the level of skeletal metastases for a longer term (or at least maintain the same level without increase). In contrast, leuprolide was less effective in the short term, and much less effective in the long term than degarelix. Similar results were obtained for the 240/160 mg dose of degarelix.

Figure 2:
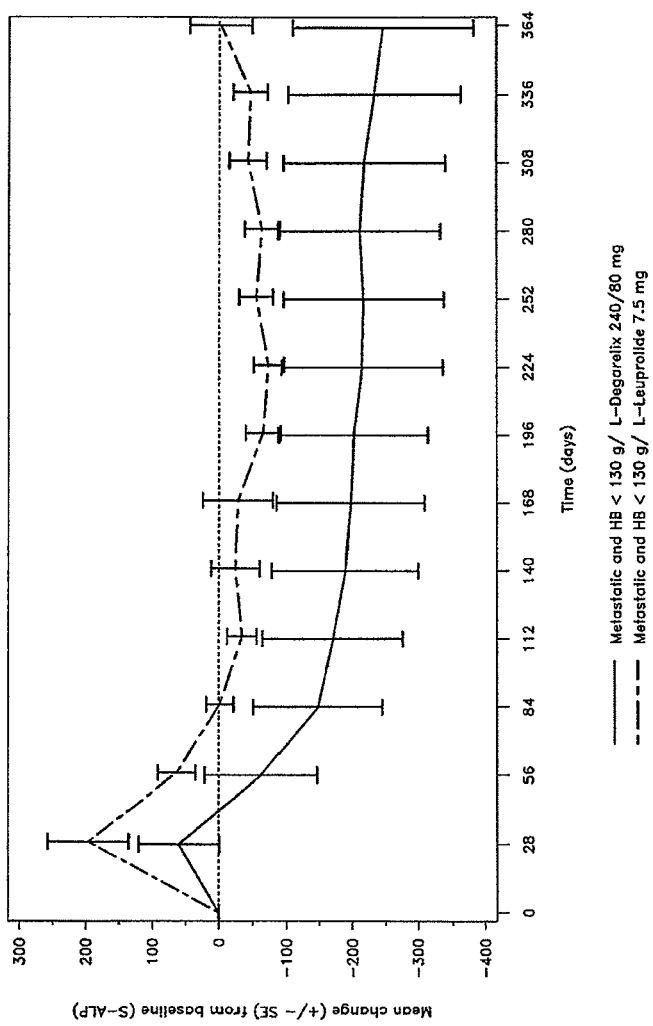
FIG. 2 is a graphical representation showing the mean change in baseline S-ALP levels, versus time, for the Metastatic (+Hb<130 g/L) subpopulation using degarelix (240/80 mg), degarelix (240/160 mg) and leuprolide (7.5 mg) treatments.

This effect is further enhanced in patients with metastatic disease and a haemoglobin (Hb) content of Hb<130 g/L, when compared with metastatic disease overall (see Table 2, and FIG. 2). Bone metastases affect bone marrow and a patient with bone metastasis may become anaemic. A lower than normal Hb in patients with bone metastasis is indicative of greater degree of metastasis (in other words, is indicative of more serious disease). Table 2 and FIG. 2 demonstrate that the long term suppression of S-ALP by degarelix was even more effective in this sub-population having more serious disease.

Figure 4:
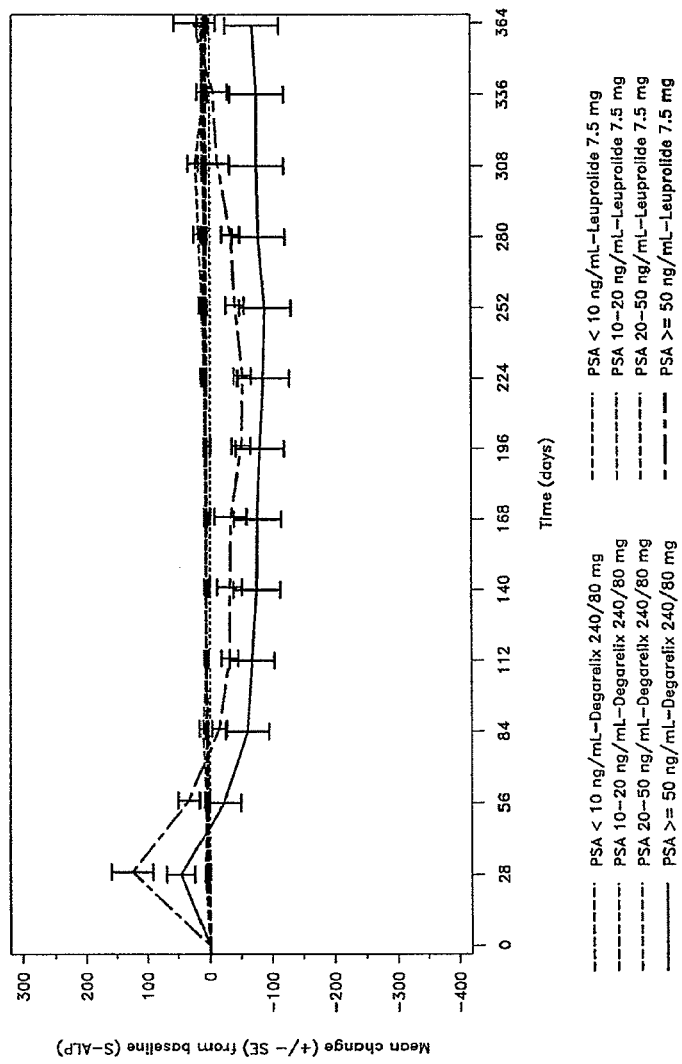
FIG. 4 is a graphical representation comparing the mean change in baseline S-ALP values, versus time, in subjects having PSA levels of <10 ng/mL, 10-20 ng/mL, 20-50 ng/mL, and >50 ng/mL, using degarelix (240/80 mg) and leuprolide (7.5 mg) treatments.

In patient groups with baseline PSA≤50 ng/mL, a general trend towards small increases in S-ALP levels was observed in both treatment groups over time. However, a different trend is seen in patients with baseline PSA≥50 ng/mL. Table 2 (2nd section) compares the S-ALP values (IU/L) for the Baseline PSA (<10 ng/mL), (10-20 ng/mL), (20-50 ng/mL), (>50 ng/mL) populations, using degarelix (240/80 mg) and leuprolide (7.5 mg) treatments. The same pattern of S-ALP response as described in FIG. 1 was seen in patients with baseline PSA≥50 ng/mL (see FIG. 4 and Table 2, 2nd section). Initial reductions were not maintained with leuprolide, with levels finishing above baseline by the study end (e.g., at 364 days) reflecting bone lesions in these patients. These initial decreases in ALP levels were, by contrast, maintained throughout the study using degarelix (240/80 mg treatment regimen). These results indicate that degarelix may be particularly effective in treating subjects (patients) having prostate cancer with baseline PSA≥50 ng/mL.

TABLE 2

S-ALP values (IU/L) for the Localized, Locally advanced, Metastatic populations, and Metastatic (Hb < 130 g/L) subpopulations, using Degarelix (240/80 mg) and Leuprolide (7.5 mg) treatments.

S-ALP values (IU/L)

| | Degarelix 240/80 mg (n = 207) | | | | | Leuprolide 7.5 mg (n = 201) | | | | |
|---|---|---|---|---|---|---|---|---|---|---|
| | | | Mean change from baseline | | | | | Mean change from baseline | | |
| | N | Mean Baseline | Day 112 | Day 224 | Day 364 | N | Mean Baseline | Day 112 | Day 224 | Day 364 |
| Disease stage (a) | | | | | | | | | | |
| Localized | 68 | 56 | +5 | +8 | +10 | 62 | 56 | +5 | +7 | +9 |
| Locally advanced | 64 | 57 | +6 | +7 | +10 | 52 | 62 | −1 | −1 | +6 |
| Metastatic | 37 | 200 | −90 | −100 | −90 | 47 | 150 | −20 | −50 | 0 |
| Metastatic (Hb < 130 g/L) | 27 | 300 | −160 | −200 | −230 | 28 | 190 | −30 | −70 | −10 |
| Mean Baseline PSA (b) | | | | | | | | | | |
| <10 ng/mL | 54 | 56 | +4.5 | +5.5 | +7 | 63 | 56 | +4.5 | +6 | +7.5 |
| 10-20 ng/mL | 52 | 55 | +5 | +8 | +13 | 44 | 55 | +5 | +8 | +8 |
| 20-50 ng/mL | 52 | 64 | +5 | +7.5 | +4.5 | 38 | 64 | +5 | +8.5 | +11 |
| >50 ng/mL | 48 | 170 | −60 | −70 | −60 | 55 | 150 | −40 | −60 | +10 |

Section (a) of Table 2 shows the S-ALP values (IU/L) for the localized, locally advanced, metastatic populations and metastatic (Hb<130 g/L) subpopulation, using degarelix (240/80 mg) and leuprolide (7.5 mg) treatments.

Section (b) of Table 2 shows the S-ALP values (IU/L) for the baseline PSA (<10 ng/mL), (10-20 ng/mL), (20-50 ng/mL), (>50 ng/mL) populations, using degarelix (240/80 mg) and leuprolide (7.5 mg) treatments.

Conclusions:

Patients with metastatic disease and/or those with PSA levels≥50 ng/mL at baseline experienced greater reductions in S-ALP levels with degarelix than leuprolide. More significantly, the rise (or return to baseline level) in S-ALP with leuprolide late in the study, indicating return of metastatic activity, was not observed with degarelix (240/80 mg) until much later. Conversant with this finding was the observation that patients in the degarelix group did not display signs of therapy failure late in the year's treatment, as indicated by significantly lower ALP levels at day 364. Finally, this effect is further enhanced in patients with metastatic disease and exhibiting a haemoglobin content of Hb<130 g/L, when compared with metastatic disease overall. These results thus indicate that degarelix may be able to reduce and/or maintain the level of skeletal metastases better than leuprolide.

Example 2

PSA Failure in Prostate Cancer Patients Treated with Degarelix Versus Leuprolide This example provides additional PSA level analyses from the phase III clinical trial CS21 (described herein), which examined the efficacy and safety of degarelix compared with leuprolide over 12 months of prostate cancer treatment. In particular, analysis of a secondary endpoint termed PSA failure revealed a surprisingly advantageous effect of degarelix treatment as compared to leuprolide treatment, particularly for patients with metastatic stage prostate cancer.

Prostate-specific antigen (PSA) is a commonly used marker in the diagnosis of prostate cancer and has more recently also been used to monitor response to treatment as well as disease recurrence and progression (Fleming et al. (2006) *Nat. Clin. Pract. Oncol.* 3: 658-67; Lilja, et al. (2008) *Nat. Rev. Cancer* 8: 268-78). In general, higher levels of PSA are associated with more severe forms of prostate cancer, with metastatic stage prostate cancer being associated with the highest levels of PSA (e.g., >50 ng/mL). Accordingly, rising PSA levels in patients undergoing prostate cancer treatment are associated with incomplete or failed efficacy of the treatment.

For this analysis, PSA failure (a secondary endpoint) was defined as two consecutive increases in PSA of 50% and ≥5 ng/mL compared with nadir. The time to PSA failure was defined as the number of days from first dosing to where an increase in serum PSA of ≥50% from nadir and ≥5 ng/mL, measured on two consecutive occasions at least two weeks apart, was noted. The second occasion was the time point of meeting the criterion. PSA failure rates were also analyzed by disease stage and baseline PSA level. In these analyses, the focus was on a comparison of degarelix 240/80 mg versus leuprolide 7.5 mg as this is the degarelix dose now approved by the FDA for the treatment of advanced prostate cancer.

The incidence of PSA failure was lower in the degarelix 240/80 mg group compared with the other two treatment groups. The probability of completing the study without experiencing PSA failure by day 364 was highest for the degarelix 240/80 mg group (91.1%; 95% CI: 85.9-94.5). The observed day 364 probability for leuprolide 7.5 mg was 85.9% (95% CI: 79.9-90.2).

PSA Failure—By Baseline Disease Stage

Figure 5:
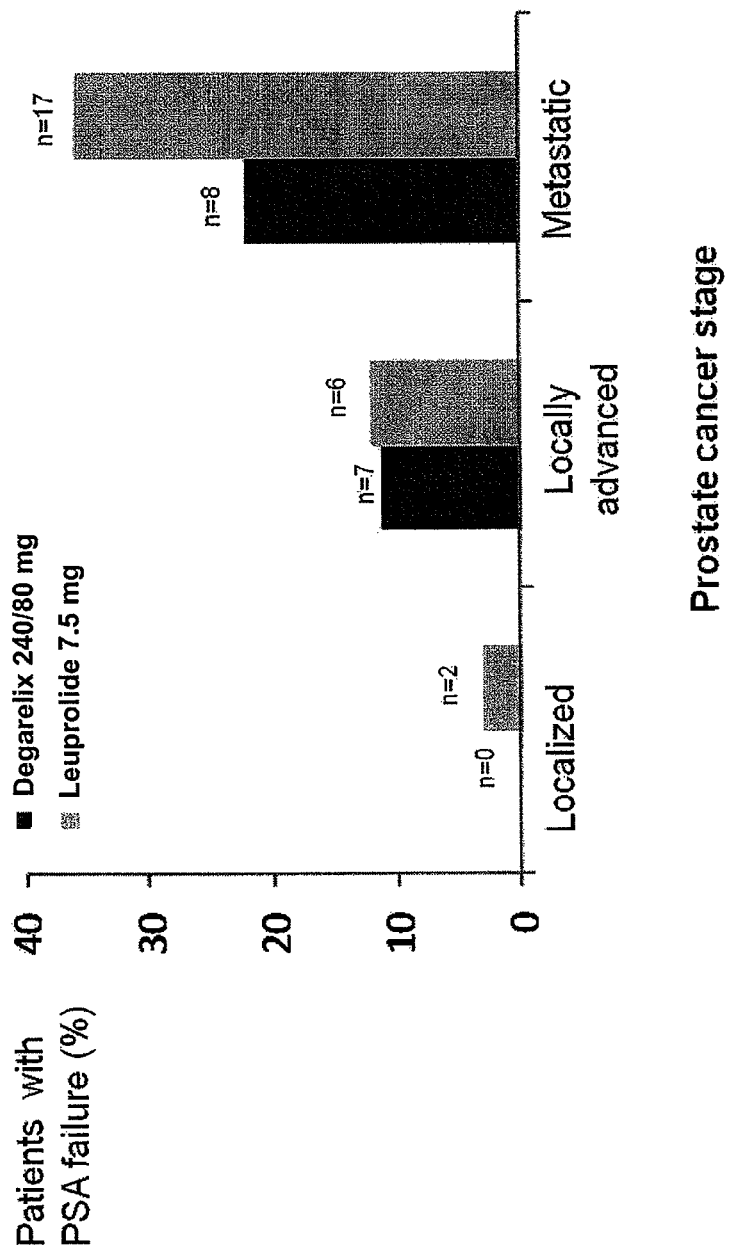
FIG. 5 is a graphical representation showing the incidence of PSA failure in subjects with baseline localized, locally advanced, and metastatic prostate cancer stages, using degarelix (240/80 mg) and leuprolide (7.5 mg) treatments.

PSA failure occurred more frequently in patients with advanced disease, across all treatment groups; the majority of PSA failures occurred in patients with metastatic disease at baseline (FIG. 5). In this subgroup of patients, a smaller proportion of PSA failures were observed during degarelix 240/80 mg treatment compared with leuprolide (21.6% vs 36.2%; p=0.1559). Accordingly, the degarelix treatment protocol provides an effective treatment for metastatic stage prostate cancer as measured by a reduced incidence of PSA failure.

PSA Failure—By Baseline PSA Level

Figure 6:
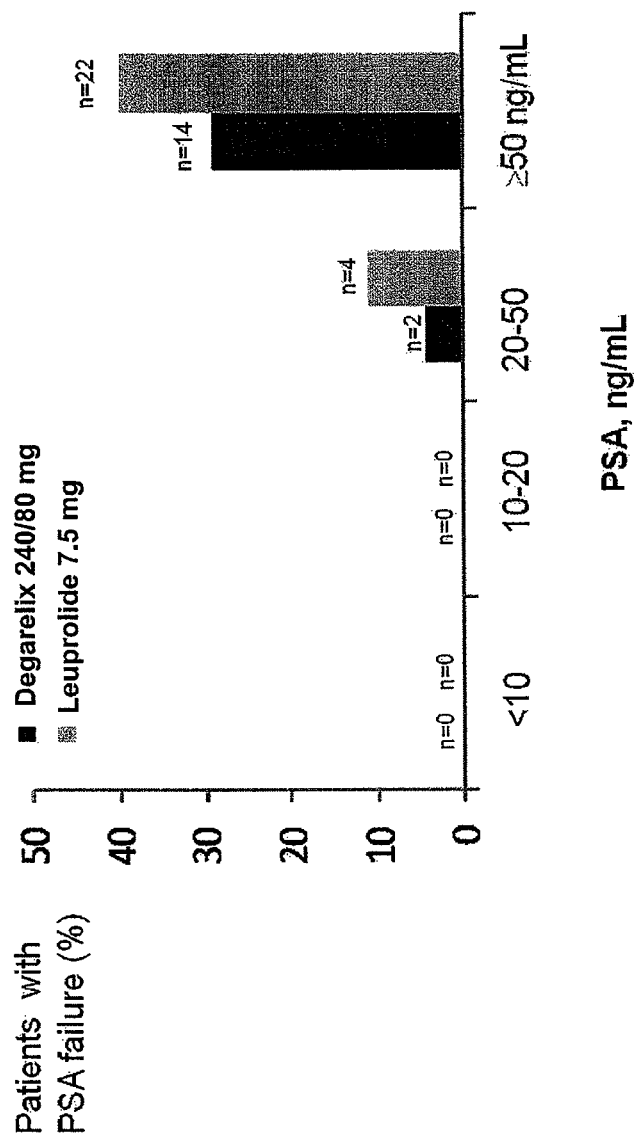
FIG. 6 is a graphical representation showing the incidence of PSA failure in subjects with baseline PSA levels of <10 ng/mL, 10-20 ng/mL, 20-50 ng/mL, and ≥50 ng/mL, using degarelix (240/80 mg) and leuprolide (7.5 mg) treatments.

PSA failure occurred more frequently in patients with higher baseline PSA level, across all treatment groups; the majority of PSA failures occurred in patients with baseline PSA>50 ng/mL (FIG. 6). In this subgroup of patients, a smaller proportion of PSA failures were observed during degarelix 240/80 mg treatment compared with leuprolide (29.2% vs 40.0%; p=0.10). Similarly, fewer patients with baseline PSA 20-50 ng/mL had PSA failure during degarelix treatment. Accordingly, the degarelix treatment protocol provides an effective treatment as measured by a reduced incidence of PSA failure in subjects with advanced stage prostate cancer, as reflected in baseline PSA levels of >50 ng/mL.

Example 3

Clinical Study of Degarelix for the Treatment of Prostate Cancer

In this example, an open-label, multi-center, randomized, parallel-group study was conducted to investigate the efficacy and safety of degarelix one month dosing regimens using either of two different once-a-month dosing regimens, 160 mg (40 mg/mL) or 80 mg (20 mg/mL). These degarelix dosing regimens were compared to leuprolide at 7.5 mg in patients with prostate cancer requiring androgen ablation therapy.

The study also investigated whether degarelix is safe and effective with respect to achieving and maintaining testosterone suppression to castrate levels, evaluated as the proportion of patients with testosterone suppression≤0.5 ng/mL during 12 months of treatment. The study assessed serum levels of testosterone and prostate-specific antigen (PSA) during the first 28 days of treatment using a degarelix dosing regimen as compared to leuprolide 7.5 mg. The study further compared the safety and tolerability using a degarelix dosing regimen compared to treatment with leuprolide 7.5 mg, and, further, compared testosterone, luteinizing hormone (LH), follicle-stimulating hormone (FSH), and PSA response with a degarelix dosing regimen compared to leuprolide 7.5 mg. The study further compared patient reported outcomes (quality of life factors and hot flushes) using a degarelix dosing regimen as compared to leuprolide 7.5 mg during treatment. The study also evaluated the pharmacokinetics of the degarelix dosing regimens investigated. Finally, the study examined the effects of using the degarelix treatment on patients suffering from different stages of cancer.

Study Design

A total of 620 patients were randomized 1:1:1 to one of three treatment groups. Of these, 610 patients (mean age 72 years, median PSA 19.0 ng/mL) were administered degarelix. Ten randomized patients withdrew from the study before dosing.

Patients in two treatment groups received a degarelix starting dose of 240 mg at a concentration of 40 mg/mL (240@40) on day 0 administered as two equivalent subcutaneous (s.c.) injections of 120 mg each. Thereafter, patients received 12 additional single s.c. degarelix doses of either 80 mg at a concentration of 20 mg/mL (80@20: degarelix 240/80 mg group) or 160 mg at a concentration of 40 mg/mL (160@40: degarelix 240/160 mg group) administered s.c. every 28 days. In the third treatment group, patients received active treatment with leuprolide 7.5 mg on day 0 and every 28 days administered as a single intramuscular (i.m.) injection. For patients receiving treatment with leuprolide 7.5 mg, bicalutamide could be given as clinical flare protection at the investigator's discretion.

Patients were stratified according to geographic region (Central and Eastern Europe, Western Europe and The Americas) and body weight (<90 kg and ≥90 kg).

Degarelix 240/160 mg Group

This group received an initial dose of 240 mg at a concentration of 40 mg/mL (240@40) on day 0. This starting dose was administered as two equivalent subcutaneous (s.c.) injections of 120 mg each. The group then received 12 maintenance doses of 160 mg at a concentration of 40 mg/mL (160@40) as single s.c doses of degarelix every 28 days.

Degarelix 240/80 mg Group

This group also received an initial dose of 240 mg at a concentration of 40 mg/mL (240@40) on day 0. This starting dose was administered as two equivalent s.c. injections of 120 mg each. The group then received 12 maintenance doses of 80 mg at a concentration of 20 mg/mL (80@20) as single s.c doses of degarelix every 28 days.

Leuprolide 7.5 mg Group

This group received the reference therapy leuprolide 7.5 mg. This treatment was administered as a single intramuscular (i.m.) injection, once every 28 days starting at day 0. These treatment regimens are summarized in Table 3 below.

TABLE 3

Treatment Methodology

| Treatment Group | Starting Dose | Maintenance Doses |
|---|---|---|
| Degarelix 240/160 mg | 240@40 (as 2 doses on day 0) | 160@40 (as 12 single doses, one every 28 days) |
| Degarelix 240/80 mg | 240@40 (as 2 doses on day 0) | 80@20 (as 12 single doses, one every 28 days) |
| Leuprolide 7.5 mg | 7.5 mg administered at day 0 and every 28 days via single intramuscular injection. Bicalutamide was given at the Investigator's discretion. | |

Patients were monitored on an ongoing basis and visited the clinic at monthly intervals up to one year. Patients were observed clinically for at least 1 hour after each administration of study drug. Patients who completed the study and met appropriate criteria were offered the opportunity to receive long-term treatment and support in an extension study.

A total of 807 patients were screened and 620 patients were randomized 1:1:1 into three treatment groups, degarelix 240/160 mg, degarelix 240/80 mg and leuprolide 7.5 mg. Of the 620 patients randomized, 610 patients actually received study medication including 202, 207 and 201 patients in the degarelix 240/160 mg, degarelix 240/80 mg and leuprolide 7.5 mg treatment groups, respectively. A total of 504 patients completed the study.

Diagnosis and Criteria for Study Inclusion

Males aged 18 years and over with histologically confirmed (Gleason graded) adenocarcinoma of the prostate (all stages), in whom androgen ablation treatment was indicated (except for neoadjuvant hormonal therapy) were eligible to participate. Signed informed consent was obtained before any study-related activity occurred. Patients were to have a baseline testosterone level>1.5 ng/mL and a PSA level of ≥2 ng/mL at the time of screening. Patients with rising PSA after having undergone prostatectomy or radiotherapy with curative intent could be included in the study. Patients were required to have an ECOG score of ≤2 and a life expectancy of at least 12 months. Previous or present hormonal management of prostate cancer (surgical castration or other hormonal manipulation, e.g. GnRH agonists, GnRH antagonists, anti-androgens, or estrogens) resulted in exclusion from the study. However, in patients having undergone prostatectomy or radiotherapy with curative intention, neoadjuvant hormonal treatment was accepted for a maximum duration of 6 months provided that this treatment had been terminated for at least 6 months prior to the screening visit. Concurrent treatment with a 5-α-reductase inhibitor also resulted in exclusion from the study. Patients who were candidates for a curative therapy (i.e. radical prostatectomy or radiotherapy) were excluded. Patients with histories of severe hypersensitivity reactions or clinically significant disorders (other than prostate cancer) that might affect the conclusion of the study as judged by the investigator were not eligible to enter into the study. Patients with a marked baseline prolongation of QT/QTcF interval (>450 msec) or that had used concomitant medications that may prolong QT/QTcF interval or who had a history of additional risk factors for Torsade de Pointes ventricular arrhythmias were excluded. Patients who had elevated serum ALT or total bilirubin levels above upper level of normal range at the screening visit or who had known or suspected hepatic, symptomatic biliary disease were also excluded. Patients were also excluded if they had a known hypersensitivity to any component of the investigational products. In addition, patients with any form of cancer within the last five years, with the exception of prostate cancer and surgically removed basal or squamous cell carcinoma of the skin, were excluded from the study. Patients who had a mental incapacity or language barriers precluding adequate understanding or co-operation were also ineligible to participate in the study. No other investigational drug was to be administered within 28 days preceding the screening visit.

Duration of Treatment

Patients in the degarelix treatment groups received a starting dose of 240@40 on day 0 and 12 maintenance doses of 160@40 (degarelix 240/160 mg group) or 80@20 (degarelix 240/80 mg group) every 28 days. Administration of degarelix took place on day 0, day 28 (±2 days) and every 28 day (±7 days) thereafter until the end of study visit, i.e., day 364 (±7 days). Patients who completed the study and met appropriate criteria were offered the opportunity to receive long-term treatment and support in an extension study.

Patients in the reference therapy group received treatment with leuprolide 7.5 mg on day 0 and every 28 days thereafter for 12 maintenance doses. Patients who completed the study received thirteen doses in total. Patients who completed the study and met appropriate criteria were offered a switch to degarelix treatment in a continuing study. These patients were randomized to degarelix treatment 240/80 mg or 240/160 mg. On day 0 of the study, patients previously treated with leuprolide 7.5 mg in study CS21 received a 240 mg (40 mg/mL) degarelix starting dose followed by monthly maintenance doses of either 80 mg (20 mg/mL) or 160 mg (40 mg/mL).

Patients in the comparator group were treated with leuprolide 7.5 mg pre-filled, dual-chamber syringe for intramuscular (i.m.) injection. Patients received leuprolide 7.5 mg on day 0 and every 28 days subsequently, administered as a single i.m. injection. At the investigator's discretion, bicalutamide could be given as clinical flare protection.

Criteria for Evaluation of Efficacy

In an aspect of the invention, the composition (or medicament) may be for treatment wherein the subject has at least a 95% likelihood of maintaining a therapeutically low serum testosterone level of less than or equal to 0.5 ng/mL by day 28 of treatment, for example wherein the subject has at least a 95% likelihood of maintaining a therapeutically low serum testosterone level of less than or equal to 0.5 ng/mL from day 28 to day 364 of treatment.

The composition (or medicament) may be for treatment wherein the subject has at least a 60% decrease (for example at least a 75% decrease) in prostate specific antigen (PSA) by day 28 of treatment. The composition (or medicament) may be for treatment with at least an 80% likelihood of maintaining a prostate specific antigen (PSA) level of less than 5 mg/mL during treatment.

The primary efficacy endpoint was the probability of testosterone levels remaining ≤0.5 ng/mL from day 28 through day 364.

The secondary efficacy endpoints were: the proportion of patients with testosterone surge during the first 2 weeks of treatment; the proportion of patients with testosterone level≤0.5 ng/mL at day 3; the percentage change in PSA from baseline to day 28; the probability of testosterone≤0.5 ng/mL from day 56 through day 364; the levels of serum testosterone, LH, FSH and PSA over time through the study; the time to PSA failure, defined as two consecutive increases of 50%, and at least 5 ng/mL as compared to nadir; degarelix concentration over the first month and trough levels at day 308 and 336; the frequency and size of testosterone increases at day 255 and/or 259 compared to the testosterone level at day 252; the quality of life on days 0, 28, 84, 168 and end of study visit; the frequency and intensity of hot flushes experienced (scored daily from study start until end of study visit). In addition, two further secondary endpoints were added: the probability of sufficient testosterone response from day 28 through day 364 (a patient was considered to have insufficient testosterone response if he had one testosterone value>1.0 ng/mL or two consecutive testosterone values>0.5 ng/mL at day 28 onwards); and the percentage change in PSA from baseline to day 14.

Criteria for Evaluation of Safety

The safety variables for this study were assessed on the following: the frequency and severity of adverse events (AEs); the presence of clinically significant changes in laboratory parameters (clinical chemistry, hematology and urinalysis); changes in electrocardiograms (ECGS) and vital signs; changes detected by physical examination; and body weight.

Body weight was measured at screening and the end of study visit. Height (without shoes) was measured at screening. Body mass index (BMI) is defined as the individual's body weight divided by the square of their height. The formulas universally used in medicine produce a unit of measure of $kg/m^2$. Body mass index may be accurately calculated using any of the formulas known in the art.

Statistical Methods

All statistical analyses were performed, and summary statistics calculated, using statistical analysis software SAS™ version 9 or higher. The populations for analysis were:

The intention-to-treat (ITT) analysis set included all randomized patients who received at least one dose of degarelix.

The per protocol (PP analysis set) comprised all the ITT analysis set without any major protocol violations.

The safety population was identical to the ITT analysis set, and therefore all safety analyses were performed on the ITT analysis set.

The primary efficacy endpoint was analyzed for both the ITT and PP analysis sets, with the ITT analysis set considered primary. The primary efficacy endpoint was analyzed using the Kaplan Meier method. For each of the three treatment groups, testosterone response rates with 95% confidence interval (CI) were calculated by log-log transformation of survivor function. Differences between the degarelix treatment groups and leuprolide 7.5 mg were assessed using a 97.5% CI calculated by normal approximation using pooled standard error.

To assess the efficacy of degarelix, two hypotheses were tested:

(1) The Food & Drug Administration (FDA) criterion was to determine whether the lower bound of the 95% confidence interval (CI) for the cumulative probability of testosterone≤0.5 ng/mL from day 28 to day 364 was no lower than 90%.

(2) The European Medicines Agency (EMEA) criterion was to determine whether degarelix was non-inferior to leuprolide 7.5 mg with respect to the cumulative probability of testosterone≤0.5 ng/mL from day 28 to day 364. The non-inferiority limit for the difference between treatments (degarelix versus leuprolide 7.5 mg) was −10 percentage points.

All secondary efficacy endpoints were analyzed for both the ITT and PP analysis sets, unless otherwise stated. The proportion of patients with testosterone surge during the first 2 weeks of treatment was analyzed using Fisher's exact test. Fisher's exact test was also used to analyze the proportion of patients with testosterone level≤0.5 ng/mL at day 3. The percentage change in PSA from baseline to day 28 endpoint was analyzed by a Wilcoxon test. For both Fisher's exact test and the Wilcoxon test, separate data presentations were made by treatment group, geographic region, weight strata (<90 kg, ≥90 kg) and for the leuprolide 7.5 mg subgroup.

The secondary endpoints, probability of testosterone≤0.5 ng/mL from day 56 through day 364, time to PSA failure, and probability of sufficient testosterone response from day 28 through day 364 were analyzed by the Kaplan-Meier method.

Efficacy Results

The primary objective of this study was to demonstrate the effectiveness of degarelix in achieving and maintaining testosterone suppression to castrate levels, evaluated as the proportion of patients with testosterone suppression≤0.5 ng/mL during 12 months of treatment.

Figure 7:
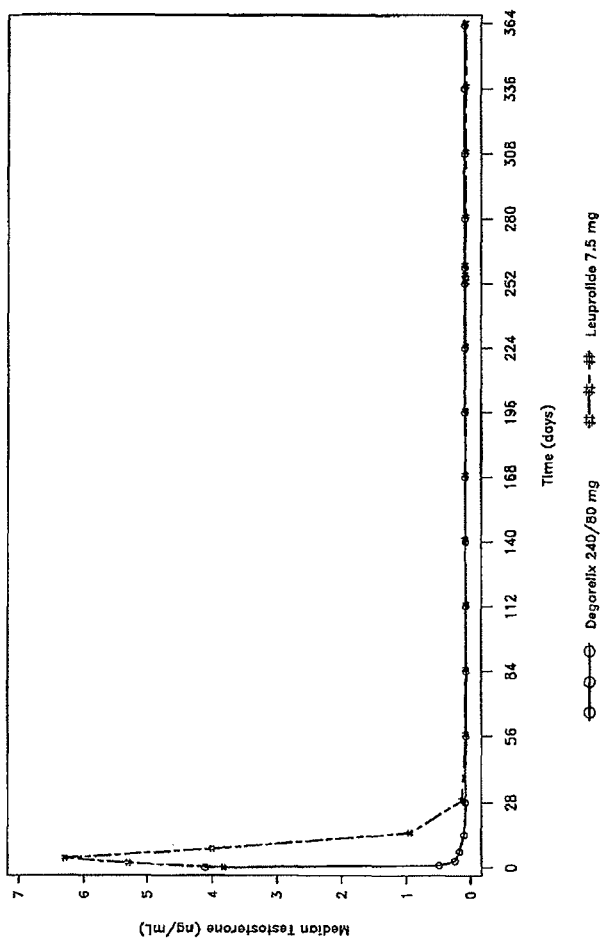
FIG. 7 is a graphical representation showing the decrease in median testosterone levels from day 0 to day 364, using degarelix (240/80 mg) and leuprolide (7.5 mg) treatments.

The results show that degarelix delivered at the 240/80 mg dosing regimen produced a rapid and effective suppression in testosterone levels, which remained low throughout the 364 day period of treatment (FIG. 7).

Kaplan-Meier estimates of the probabilities of testosterone≤0.5 ng/mL from day 28 to day 364 were 98.3%, 97.2% and 96.4% for the degarelix 240/160 mg, degarelix 240/80 mg and leuprolide 7.5 mg groups, respectively. For all three treatment groups, the lower bound of the 95% CI was above the pre-specified 90% threshold. Treatment with degarelix was demonstrated to be non-inferior to leuprolide 7.5 mg therapy with respect to the probability of testosterone≤0.5 ng/mL from day 28 to day 364. For both degarelix treatment groups, the entire 97.5% CI for the difference in probability compared with the leuprolide 7.5 mg group was greater than the non-inferiority limit of −10 percentage points. Thus, the study fulfilled the FDA and EMEA criteria for efficacy.

The robustness of the results for the primary efficacy endpoint was supported by an observed cases analysis, which produced similar estimates of the overall proportion of patients with testosterone<0.5 ng/mL from day 28 to day 364 for the degarelix 240/160 mg, degarelix 240/80 mg and leuprolide 7.5 mg groups of 98.2%, 97.0% and 96.0%, respectively. The findings of the primary analysis were further supported by a secondary efficacy analysis of the probability of testosterone≤0.5 ng/mL from day 56 to day 364.

Figure 8:
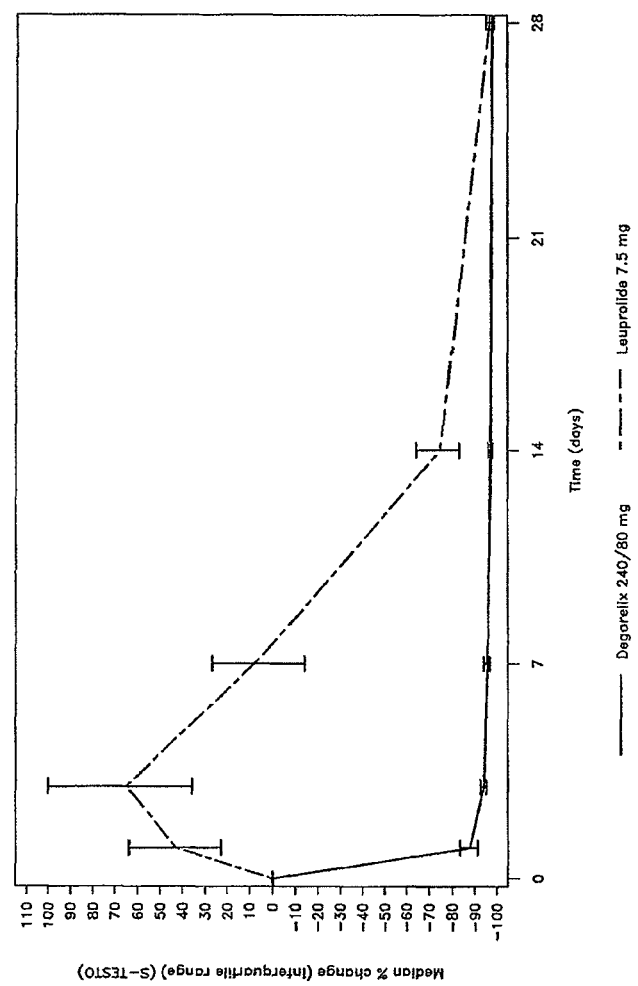
FIG. 8 is a graphical representation showing the median percentage change in testosterone level from day 0 to day 28, using degarelix (240/80 mg) and leuprolide (7.5 mg) treatments.

As expected, a significantly higher proportion of patients in the leuprolide 7.5 mg group (80.1%) had a testosterone surge (increase ≥15% from baseline) during the first two weeks of treatment compared with the pooled degarelix groups (0.2%: one patient) (p<0.0001, Fisher's exact test). The patient treated with degarelix can be considered to be an artifact as this patient had low testosterone at baseline (0.0065 ng/mL) thus a surge from such a low baseline value was not remarkable. Conversely, 96% of patients receiving degarelix exhibited testosterone suppression on day 3 compared with no patients in the leuprolide 7.5 mg group (p<0.0001, Fisher's exact test). As shown in FIGS. 7 and 8, the degarelix 240/80 mg dosing regimen rapidly and efficiently suppressed testosterone levels, while leuprolide 7.5 mg acted much more gradually and only after an initial testosterone surge.

Figure 9:
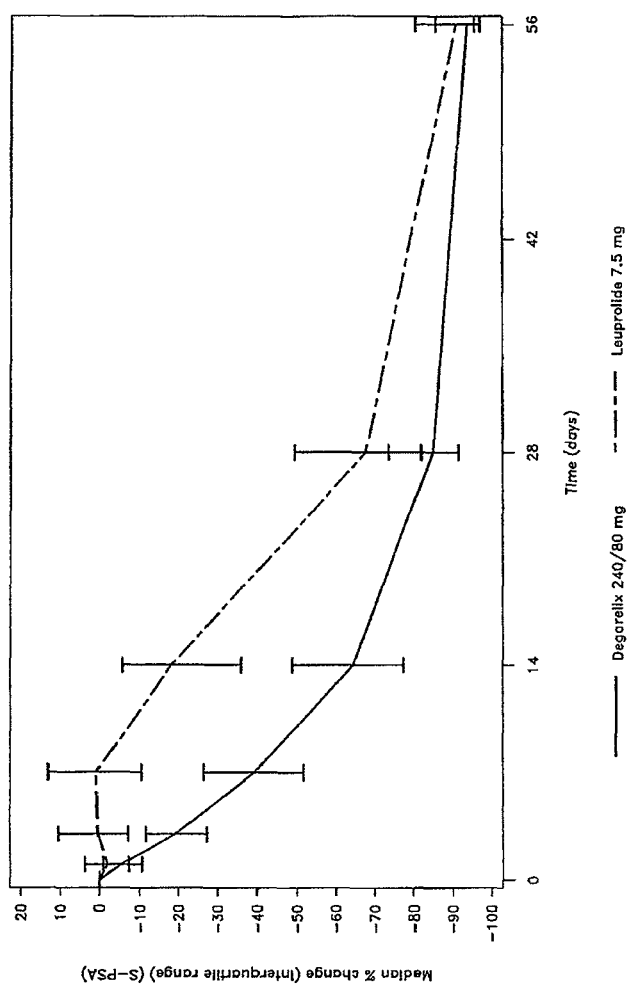
FIG. 9 is a graphical representation showing the median percentage change in PSA level from day 0 to day 56, using degarelix (240/80 mg) and leuprolide (7.5 mg) treatments.

As shown in FIG. 9, the degarelix 240/80 mg dosing regimen also produced a more rapid and efficient reduction in PSA levels than did treatment with leuprolide 7.5 mg. A rapid reduction in PSA levels was observed for patients treated with degarelix. In contrast, PSA levels in the leuprolide 7.5 mg group reached a plateau during the first week of treatment before decreasing exponentially to suppressed levels. There was a significantly greater reduction in median PSA levels from baseline that was observed on day 14 and day 28 for degarelix patients compared with leuprolide 7.5 mg patients (p<0.0001, Wilcoxon test). The probability of a PSA observation from the pooled degarelix groups being less than one from the leuprolide 7.5 mg group was slightly higher on day 14 (0.82) than on day 28 (0.70). The probability of completing the study without experiencing PSA failure was highest in the degarelix 240/80 group (91.2%) and slightly lower (~85.8%) for both the degarelix 240/160 mg and leuprolide 7.5 mg groups, although this difference was not statistically significant.

Anti-androgen therapy, as per protocol, was given to 22 patients in the leuprolide 7.5 mg group at the start of treatment for flare protection. PSA data for these patients showed a greater median percentage change from baseline at day 14 (61.7% reduction) and day 28 (89.1%) compared to those patients in the leuprolide 7.5 mg group who did not receive anti-androgen therapy, where the percentage reduction was 15.3% and 61.7% at days 14 and 28, respectively. It should be noted that the median percentage change in PSA levels in the leuprolide plus antiandrogen patients was similar to those patients treated with degarelix, thereby confirming that degarelix is more effective than conventional GnRH agonist therapy at suppressing PSA at the start of treatment. Degarelix does not require additional concomitant medication as prophylaxis for flare, yet a starting dose of 240 mg has a similar effect on PSA levels as the combination of GnRH agonist plus anti-androgen.

Figure 10:
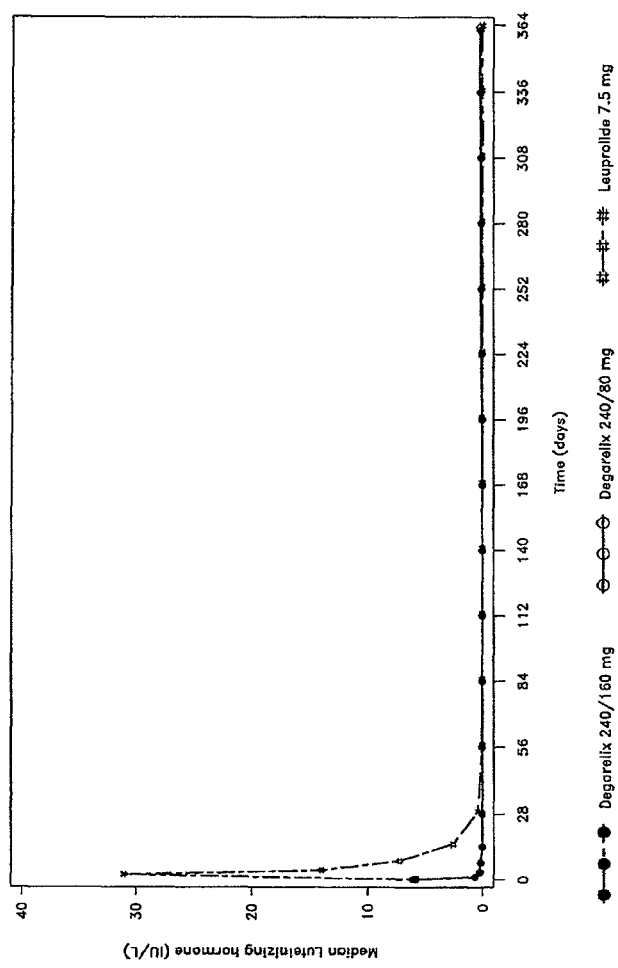
FIG. 10 is a graphical representation showing the median LH level from day 0 to day 364, using degarelix (240/160 mg), degarelix (240/80 mg) and leuprolide (7.5 mg) treatments.

The profiles for serum levels of LH over time were similar to those observed for testosterone. Following administration of degarelix, median LH levels for the ITT analysis set decreased rapidly and were <0.7 IU/L on day 1, a decrease of approximately 88% from baseline. For both degarelix treatment groups median LH levels remained suppressed until the end of the study on day 364. In contrast, a surge in median LH levels was observed for patients in the leuprolide 7.5 mg group, which peaked at 31.0 IU/L on day 1 (>400% increase from baseline) before decreasing exponentially to 0.035 IU/L by day 56 and remaining at this level until day 364 (see FIG. 10).

Figure 11:
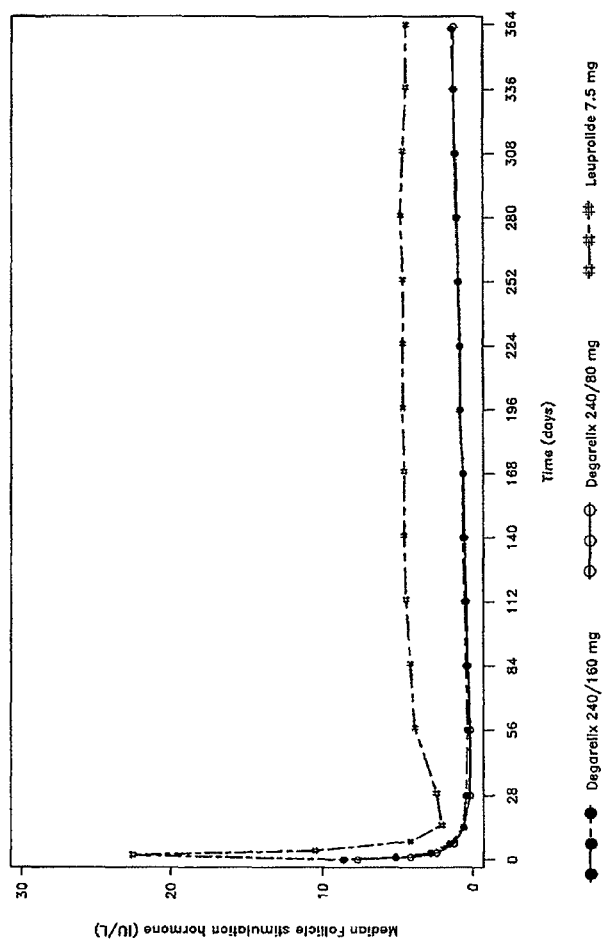
FIG. 11 is a graphical representation showing the median FSH level from day 0 to day 364, using degarelix (240/160 mg), degarelix (240/80 mg) and leuprolide (7.5 mg) treatments.

A rapid decrease in FSH levels was also observed in patients treated with degarelix. Administration of degarelix resulted in a reduction in median FSH levels to ≤1.5 IU/L by day 7, a >80% decrease from baseline. For both degarelix treatment groups median FSH levels remained suppressed until the end of the study on day 364. For patients in the leuprolide 7.5 mg group there was an initial surge in FSH levels similar to that observed for LH levels which peaked at 22.5 IU/L on day 1 (146% increase from baseline) before decreasing exponentially to 2.0 IU/L by day 14. Median FSH subsequently increased around day 56 to a plateau of approximately 4.40 IU/L and stayed there until day 364 (see FIG. 11).

The pharmacodynamic profile for degarelix was characteristic of a GnRH antagonist with serum levels of testosterone, LH and FSH suppressed rapidly. In contrast, for patients in the leuprolide 7.5 mg group, serum levels of testosterone, LH and FSH increased rapidly within the first week of treatment before falling to suppress levels. (See FIGS. 7, 8, 10 and 11).

Safety Results

Safety and tolerability were evaluated by observed and reported treatment-emergent AEs, including injection site reactions, haematological, clinical chemistry and urinalysis laboratory parameters, vital signs/clinical observations, and body weight measurements and physical examination, ECGs and concomitant medication.

Safety parameters were evaluated for all patients included in the ITT analysis set, comprising all 610 randomized patients who received at least one dose of study medication.

The invention claimed is:

1. A method of treating metastatic stage prostate cancer in a subject, the method comprising:
identifying a subject with metastatic stage prostate cancer comprising measuring the subject's baseline serum alkaline phosphatase (S-ALP) level; and
reducing the subject's S-ALP level with respect to the baseline level by
administering an initial dose of degarelix ranging from about 160 to about 320 mg to the subject; and
administering at least one maintenance dose of degarelix ranging from about 60 mg to about 160 mg to the subject, wherein the at least one maintenance dose is administered approximately 20 days to 36 days, after the previous dose of degarelix for a duration of treatment ranging from 20 days to 450 days; and
further, wherein the S-ALP level is reduced for the duration of treatment relative to the initial S-ALP level measured at the start of treatment.

2. The method of claim 1, wherein the initial dose of degarelix is about 240 mg, and the at least one maintenance dose of degarelix is about 80 mg administered to the subject approximately 28 days after the previous dose of degarelix.

3. The method of claim 1 wherein identifying the subject comprises measuring the baseline S-ALP level in the subject of 150 IU/L or greater.

4. The method of claim 1, wherein identifying the subject comprises measuring the baseline S-ALP level in the subject of 160 IU/L or greater.

5. The method of claim 1, wherein identifying the subject comprises measuring the baseline S-ALP level in the subject of 200 IU/L or greater.

6. The method of claim 1, wherein identifying the subject comprises measuring the baseline S-ALP level in the subject of 300 IU/L or greater.

7. The method of claim 1, wherein the treated subject's S-ALP level is reduced by at least 60 IU/L from the baseline level between day 112 and day 364 of treatment.

8. The method of claim 1, wherein the treated subject's S-ALP level is reduced by at least 50 IU/L from the baseline level between day 60 and day 364 of treatment.

9. The method of claim 1, wherein the treated subject's S-ALP level is reduced by at least 50 IU/L from the baseline level between day 364 and day 450 of treatment.

10. The method of claim 1, wherein the treated subject's S-ALP level is reduced by at least 90 IU/L from the baseline level between day 112 and day 364 of treatment.

11. The method of claim 1, wherein the treated subject's S-ALP level is reduced by at least 160 IU/L from the baseline level between day 112 and day 364 of treatment.

12. The method of claim 1, wherein the treated subject has at least a 95% likelihood of having a therapeutically low serum testosterone level of less than or equal to 0.5 ng/mL by day 28 of treatment.

13. The method of claim 1, wherein the treated subject has at least a 95% likelihood of maintaining a therapeutically low serum testosterone level of less than or equal to 0.5 ng/mL from day 28 to day 365 of treatment.

14. The method of claim 1, comprising administering from 1 to 21 maintenance doses of degarelix to the subject, wherein each maintenance dose is administered approximately 20 days to 36 days after the previous dose of degarelix.

15. A method of treating metastatic stage prostate cancer in a subject. the method comprising:
   identifying a subject with metastatic stage prostate cancer comprising measuring the subject's baseline serum alkaline phosphatase (S-ALP) level and measuring the subject's baseline prostate-specific antigen (PSA) level; and
   reducing the subject's S-ALP level with respect to the baseline level by
      administering an initial dose of degarelix ranging from about 160 mg to about 320 mg to the subject; and
      administering at least one maintenance dose of degarelix ranging from about 60 mg to about 160 mg to the subject approximately 20 days to 36 days after the previous dose of degarelix for a duration of treatment.

16. The method of claim 15, wherein identifying the subject comprises measuring the baseline S-ALP level in the subject of 150 IUIL or greater.

17. The method of claim 15, wherein identifying the subject comprises measuring the baseline S-ALP level in the subject of 160 IUIL or greater.

18. The method of claim 15, wherein the treated subject's S-ALP level is reduced by at least 60 IUIL from the baseline level between day 112 and day 364 of treatment.

* * * * *